US010273498B2

(12) United States Patent
Bull et al.

(10) Patent No.: US 10,273,498 B2
(45) Date of Patent: Apr. 30, 2019

(54) METHODS AND COMPOSITIONS TO ENHANCE PLANT BREEDING

(71) Applicant: Monsanto Technology LLC, St. Louis, MO (US)

(72) Inventors: Jason Bull, St. Louis, MO (US); David Butruille, Urbandale, IA (US); Sam Eathington, Ames, IA (US); Marlin Edwards, Davis, CA (US); Anju Gupta, Ankeny, IA (US); Richard Johnson, Urbana, IL (US); Wayne Kennard, Ankeny, IA (US); Jennifer Rinehart, Spring Green, WI (US); Kunsheng Wu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 73 days.

(21) Appl. No.: 15/433,124

(22) Filed: Feb. 15, 2017

(65) Prior Publication Data

US 2017/0156276 A1 Jun. 8, 2017

Related U.S. Application Data

(63) Continuation of application No. 14/283,630, filed on May 21, 2014, now Pat. No. 9,605,272, which is a continuation of application No. 12/640,069, filed on Dec. 17, 2009, now Pat. No. 8,754,289, which is a continuation of application No. 11/441,915, filed on May 26, 2006, now abandoned.

(60) Provisional application No. 60/685,584, filed on May 27, 2005.

(51) Int. Cl.

| | |
|---|---|
| ***A01H 5/10*** | (2018.01) |
| ***C12N 15/82*** | (2006.01) |
| ***A01H 1/02*** | (2006.01) |
| ***A01H 1/04*** | (2006.01) |
| ***A01N 57/20*** | (2006.01) |

(52) U.S. Cl.

CPC .......... *C12N 15/8275* (2013.01); *A01H 1/02* (2013.01); *A01H 1/04* (2013.01); *A01H 5/10* (2013.01); *A01N 57/20* (2013.01); *C12N 15/821* (2013.01); *C12N 15/8286* (2013.01); *Y02A 40/162* (2018.01)

(58) Field of Classification Search

None

See application file for complete search history.

(56) References Cited

U.S. PATENT DOCUMENTS

| | | | |
|---|---|---|---|
| 4,535,060 | A | 8/1985 | Comai |
| 5,110,805 | A | 5/1992 | Berner et al. |
| 5,310,667 | A | 5/1994 | Eichholtz et al. |
| 5,312,910 | A | 5/1994 | Kishore et al. |
| 5,554,798 | A | 9/1996 | Lundquist et al. |
| 5,804,425 | A | 9/1998 | Barry et al. |
| 6,248,876 | B1 | 6/2001 | Barry et al. |
| 6,462,258 | B1 | 10/2002 | Fincher et al. |
| 6,573,425 | B1 | 6/2003 | Baszczynski |
| 6,610,910 | B1 | 8/2003 | Streit et al. |
| 6,689,880 | B2 | 2/2004 | Chen et al. |
| 6,733,974 | B1 | 5/2004 | Feazel |
| 6,740,488 | B2 | 5/2004 | Rangwala et al. |
| 6,818,807 | B2 | 11/2004 | Trolinder et al. |
| 6,893,826 | B1 | 5/2005 | Hillyard et al. |
| 6,900,014 | B1 | 5/2005 | Weston et al. |
| 6,919,495 | B2 | 7/2005 | Fincher et al. |
| 7,098,170 | B2 | 8/2006 | Asrar et al. |
| 7,306,909 | B2 | 12/2007 | Krieb et al. |
| 7,405,074 | B2 | 7/2008 | Castle et al. |
| 7,405,347 | B2 | 7/2008 | Hammer et al. |
| 2002/0133852 | A1 | 9/2002 | Hauge et al. |
| 2003/0114308 | A1 | 6/2003 | DeBillot |
| 2005/0223425 | A1 | 10/2005 | Clinton et al. |
| 2005/0233905 | A1 | 10/2005 | DeBillot et al. |
| 2006/0111239 | A1 | 5/2006 | Oakley et al. |
| 2006/0223707 | A1 | 10/2006 | Baley et al. |
| 2006/0282911 | A1 | 12/2006 | Bull et al. |
| 2006/0282915 | A1 | 12/2006 | Malven et al. |
| 2006/0288447 | A1 | 12/2006 | Baley |
| 2007/0197474 | A1 | 8/2007 | Clinton et al. |

FOREIGN PATENT DOCUMENTS

| | | |
|---|---|---|
| DE | 10059609 | 6/2002 |
| WO | 1992000377 | 1/1992 |
| WO | 1999023232 | 5/1999 |
| WO | 1999031964 | 7/1999 |
| WO | 2001049104 | 7/2001 |
| WO | 2002006500 | 1/2002 |
| WO | 2002044407 | 6/2002 |
| WO | 2003013224 | 2/2003 |
| WO | 2004043150 | 5/2004 |
| WO | 2004072235 | 8/2004 |

(Continued)

OTHER PUBLICATIONS

Anderson et al.,"Rust Control in Glyphosate Tolerant Wheat Following Application of the Herbicide Glyphosate," Plant Disease, 89(11): 1136-1142 (2005).

(Continued)

*Primary Examiner* — Medina A Ibrahim

(74) *Attorney, Agent, or Firm* — James E. Davis

(57) ABSTRACT

The present invention provides breeding methods and compositions to enhance the germplasm of a plant. The methods describe the identification and accumulation of transgenes and favorable haplotype genomic regions in the germplasm of a breeding population of crop plants.

7 Claims, No Drawings

Specification includes a Sequence Listing.

(56) References Cited

FOREIGN PATENT DOCUMENTS

| | | |
|---|---|---|
| WO | 2005041669 | 5/2005 |
| WO | 2005102057 | 11/2005 |
| WO | 2006130436 | 12/2006 |
| WO | 2007017256 | 2/2007 |

OTHER PUBLICATIONS

Axelos et al., "The Gene Family Encoding the *Arabidopsis thaliana* Translation Elongation Factor EF-1 Alpha: Molecular Cloning, Characterization and Expression," Mol. Gen Genet, 219(1-2): 106-112 (1989).

Barker et al., "Nucleotide Sequence of the T-DNA Region from the Agrobacterium Tumefaciens Octopine Ti Plasmid pTi15955," Plant Mol. Biol., 2: 335-350 (1983).

Chevalier et al., "Design, Activity, and Structure of a Highly Specific Artificial Endonuclease," Molecular Cell, 10:895-905 (2002).

Coruzzi et al., "Tissue-Specific and Light-Regulated Expression of Pea Nuclear Gene Encoding the Small Subunit of ribulos-1,5-bisphosphate caroxylase," EMBO J., 3: 1671-1679 (1984).

Depicker et al., "Nopaline Synthase: Transcript Mapping and DNA Sequence," J. Mol. Appl. Genet, 1(6): 561-573 (1982).

Feng et al., "Glyphosate Inhibits Rust Diseases in Glyphosate-Resistant Wheat and Soybean," PNAS, 102(48): 17290-17295 (2005).

Franz et al., "Glyophosate: A Unique Global Herbicide," American Chemical Society, 5: 103-141 (1997).

Gepts, P., "A Comparison Between Crop Domestication, Classical Plant Breeding, and Genetic Engineering," Crop Science, 42(6): 1780-1790 (2002).

Grossbard et al., "Effects of Glyphosate on the Microflora: with Reference to the Decomposition of Treated Vegetation and Interaction with Some Plant Pathogens," The Herbicide Glyphosate, 11: 159-165, 178-182 (1985).

Harrison et al., "The Expressed Protein in Glyphosate-Tolerant Soybean, 5-enolpyruvylshikimate-3-phosphate synthase from *Agrobacterium* sp. strain CP4, is Rapidly Digested in Vitro and is not Toxic to Acutely Gavaged Mice," J. Nutr., 126(3): 728-740 (1996).

Hernandez et al., "Development of Melting Temperature-Based SYBR Green I Polymerase Chain Reaction Methods for Multiplex Genetically Modified Organism Detection," Analytical Biochemistry, 323(2): 164-170 (2003).

Klee et al., "Cloning of an *Arabidopsis thaliana* Gene Encoding 5-enolpyruvylshikimate-3-phospate synthase: Sequence Analysis and Manipulation to Obtain Glyphosate-Tolerant Plants," Mol. Gen Genet, 210(3): 437-442 (1987).

Lloyed et al., "Targeted Mutagenesis Using Zinc-Finger Nucleases in *Arabidopsis*," Proc. Natl. Acad. Sci., 102(6): 2232-2237 (2005).

Monsanto Company, "Application for Authorization to place on the market MONS 89788 Soybean in the European Union, According to Regulation (EC) No. 1829/2003 on Genetically Modified Food and Feed—Part II-Summary," Summary of the Dossier EFSA GMO NL 2006, 36: 1-31 (2006).

Office Action regarding U.S. Appl. No. 11/441,914, dated Sep. 2, 2008.

Office Action regarding U.S. Appl. No. 11/441,914, dated Jun. 16, 2008.

Padgette et al., "Site-Directed Mutagensis of a Conserved Region of the 5-enolpyruvylshikimate-3-phosphate synthase Active Site," J. Biological Chemistry, 266(33): 22364-22369 (1991).

PCT International Search Report for PCT/US2006/020323, dated Jan. 2, 2007.

PCT International Search Report for PCT/US2006/020522, dated Jan. 9, 2007.

Ramsdale et al., "Glyphosate Tank-Mixed with Insecticides or Fungicides," North Central Weed Science Society, 59: 280-283 (2002).

Response to Office Action Regarding U.S. Appl. No. 11/441,918, dated Sep. 14, 2008.

Richins et al., "Sequence of Figwort Mosaic Virus DNA (Caulimovirus Group)," Nucleic Acids Res., 15(20): 8451-8466 (1987).

Rott et al., "Detection and Quantification of Roundup Ready Soy in Foods by Conventional and Real-Time Polymerase Chain Reaction," Journal of Agricultural and Food Chemistry, 52(16): 5223-5232 (2004).

Sanogo et al., "Effects of Herbicides on *Fusarium solani f.*sp. Glycines and Development of Sudden Death Syndrome in Glyphosate-Tolerant Soybean," Amer. Phytopathological Society, 90(1): 57-66 (2000).

Smith et al., "A Combinatorial Approach to Create Artificial Homing Endonucleases Cleaving Chosen Sequences," Nucleic Acids Res., 34(22): 1-12 (2006).

Terry et al., "Event-Specific Detection of Roundup Ready Soya Using Two Different Real Time PCR Detection Chemistries," Eur. Food Res. Technol., 213: 425-431 (2001).

Windels et al., "Characterisation of the Roundup Ready Soybean Insert," Eur. Food Res. Technol., 213: 107-112 (2001).

Windels et al., "Development of a Line Specific GMO Detection Method: A Case Study," Me. Fac. Ladbouww. Univ. Gent., 65(5b): 459-462 (1999).

METHODS AND COMPOSITIONS TO ENHANCE PLANT BREEDING

BACKGROUND OF THE INVENTION

This application is a continuation of U.S. application Ser. No. 14/283,630, filed on May 21, 2014, which is a continuation of U.S. application Ser. No. 12/640,069, filed on Dec. 17, 2009, which is a continuation of U.S. application Ser. No. 11/441,915, filed May 26, 2006, which claims the benefit of U.S. Provisional Application No. 60/685,584, filed May 27, 2005, the entire text of which is specifically incorporated by reference herein.

FIELD OF THE INVENTION

The invention relates to the field of plant breeding and plant biotechnology, in particular to a transgene inserted into genetic linkage with a genomic region of a plant, and to the use of the transgene/genomic region to enhance the germplasm and to accumulate other favorable genomic regions in breeding populations.

DESCRIPTION OF RELATED ART

Breeding has advanced from selection for economically important traits in plants and animals based on phenotypic records of the individual and its relatives to the use of molecular genetics to identify genomic regions that contain the valuable genetic traits. Information at the DNA level has lead to faster genetic accumulation of valuable traits into a germplasm than that achieved based on the phenotypic data only. The development of transgenic crops has further revolutionized breeding and agricultural crop production. The outstanding success of genetically engineered crops is evident from the fact that the area of farmland devoted to transgenic crops has grown from a negligible acreage ten years ago to well over half the acreage for major crops in agriculturally important countries such as USA, Canada, Brazil and Argentina. In addition to the development of input traits, plant biotechnology also holds great promise for the future development of output traits that will directly benefit consumers, like nutritionally superior foods, such as the vitamin A enriched rice, unsaturated oils, and agricultural products of medical value to name a few. The potential for commercial success of a transgene encoding a new or improved input or output trait is a great incentive for development of novel transgenes and their deployment through breeding these genes into elite germplasm.

During the development of transgenic crop plants much effort is concentrated on optimization of the insertion and expression of the transgene, and then introgressing the transgene throughout the breeding population by classical breeding methods. The site of insertion of a transgene into the host genome has been a concern for at least two reasons; (i) the region where it inserted may modulate the level of expression of the transgene, and (ii) the insertion of the transgene may disrupt the normal function or expression of a gene near or where it has been inserted. The selection of genomic locations that are beneficial for gene integration provides for suitable levels of stable expression of an introduced gene, or genes, and generally does not negatively affect other agronomic characteristics of the crop plant.

The genomic region in which the transgene has been inserted also provides agronomic phenotypes to the crop plant. These phenotypes have their own value in a breeding program and these regions should be considered when selecting among multiple transgene insertion events. Transgene insertion events into genomic regions that are associated with improved performance with respect to an agronomic trait or multiple trait index result in an improved phenotype in the crop plant and progeny derived from the crop plant that contain the transgene and the associated improved phenotype. Selecting for the transgenic event necessarily results in selecting a segment of the host genome that surrounds it, and the improved phenotypic effect. Further improvements involve the identification of molecular markers for the tracking and maintenance of the genomic segment with the associated transgene. This is an area that has not been adequately addressed in current plant breeding with transgene insertion events.

There is a need in the art of plant breeding to identify genomic regions associated with improved performance with respect to an agronomic trait or multiple trait index that are linked with a transgene insertion event and then select for these transgene-genomic regions for dispersion into the breeding population of the crop. The present invention provides consideration to estimating the value of the genomic region and the transgene event. This value can then be used as a criterion for selecting among multiple transgenic events. A further benefit is that linkage drag around a transgene is minimized and valuable genomic regions are selected that contain the transgene for breeding into the germplasm of a crop.

SUMMARY OF THE INVENTION

The present invention provides a method of breeding with transgenic plants. In one aspect, this method comprises providing a database identifying a value of an agronomic trait for at least two distinct haplotypes of the genome for a set of germplasm. The method further comprises transforming a parent plant with recombinant DNA to produce at least two transgenic events wherein the recombinant DNA is inserted into linkage with the at least two distinct haplotypes of the genome of the parent plant. The database may then be referenced to estimate the value of the agronomic trait for the events linked to the distinct haplotypes, and transgenic event having a higher referenced breeding value may then be selected for breeding into a germplasm.

The present invention provides a method for improving plant germplasm by accumulation of one or more haplotypes in a germplasm. The method comprises inserting a transgene into a genome of a first plant, and then determining a map location of the transgene in the genome. The map location may be correlated to a linked haplotype, wherein the transgene and the haplotype comprise a T-type genomic region. The first plant may then be crossed with a second plant. The second plant may contain at least one T-type genomic region or haplotype that is different from the first plant T-type genomic region. At least one progeny plant may then be selected, the progeny plant having detectable expression of the transgene or its phenotype and comprising in its genome the T-type genomic region of the first plant and at least one T-type genomic or haplotype of the second plant. The progeny plant may be used in activities related to germplasm improvement, which can be selected from use of the plant for making breeding crosses, further testing of the plant, advancement of the plant through self fertilization, use of the plant or parts thereof for transformation, use of the plant or parts thereof for mutagenesis, and use of the plant or parts thereof for TILLING, or any combination of these.

The present invention includes a method for breeding of a crop plant, in particular a soybean or corn plant with enhanced agronomic and transgenic traits comprising a preferred T-type genomic region. A transgene of the T-type genomic region is further defined as conferring a preferred property like herbicide tolerance, disease resistance, insect or pest resistance, altered fatty acid, protein or carbohydrate metabolism, increased grain yield, increased oil, increased nutritional content, increased growth rates, enhanced stress tolerance, or altered morphological characteristics, or any combination of these.

The present invention provides a novel method for mapping at least one genomic region of insertion of a transgene. This method involves indirect mapping and does not require the establishment of a de novo population segregating for a transgene. The method comprises first identifying at least a first polymorphism between the parent lines of a mapping population in the corresponding genomic region adjacent to a transgenic insertion event in a transformed plant or line, then assaying the progeny plants of the mapping population for the polymorphism. Linkage analysis may be performed to determine a map position of the polymorphism and thereby a map location of the transgenic insertion event. The map location in the mapping population may then be correlated to a haplotype of the transformed plant and its progeny.

DESCRIPTION OF ILLUSTRATIVE EMBODIMENTS

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Rieger et al. (1991); and Lewin (1994). The nomenclature for DNA bases as set forth at 37 CFR § 1.822 is used.

As used herein, the term "corn" means *Zea mays* or maize and includes all plant varieties that can be bred with corn, including wild maize species.

As used herein, the term "soybean" means *Glycine max* and includes all plant varieties that can be bred with soybean, including wild soybean species.

As used herein, the term "comprising" means "including but not limited to".

A transgenic "event" is produced by transformation of a plant cell with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA.

The present invention overcomes the deficiencies of the current transgene breeding methods by describing a T-type genomic region, defined as a transgene and a linked haplotype genomic region, through which the genetically linked transgene and haplotype are selected and then introgressed into germplasm through breeding. The selection of the T-type genomic region is based on the estimation of a T-value that the T-type genomic region provides to the germplasm of the crop plant. The basis of the valuation distinguishes and selects improved T-type genomic regions for use in a breeding method, and selects and advances plants comprising the improved T-type genomic regions. The genomic locations for gene integration are favorable based on providing suitable levels of stable expression of an introduced gene, or genes, and for identifying transgene associations with favorable haplotype regions that also provide beneficial agronomic characteristics to the germplasm. By considering the beneficial aspects of both the transgene and the genomic region to which it is genetically linked, additional value can be built into a transgenic event and its use for developing superior germplasm. In an unexpected outcome from extensive experience in breeding with transgenic plants, the inventors have realized that additional consideration should be given to the genomic region that is linked to the transgene insertion. As a transgene is diffused by breeding methods into plant germplasm a portion of the genetic region linked to the transgene is also diffused. By giving consideration to the genetic region linked to a transgene it is possible to implement biotechnological and breeding strategies to increase the overall value of the transgene and the genetic region to which it is linked to enhance germplasm improvement and minimize the risk of advancement of less favorable genetic regions, often referred to as linkage drag.

For example, in one aspect of the present invention, T-type genomic regions of new glyphosate tolerant soybean events have been identified that comprise a glyphosate tolerance transgene with suitable levels of expression in linkage with a haplotype. The highest yielding T-type was identified as event 19788 (also referred to as MON89788) and provided for the replacement of the T-type genomic region of event 40-3-2 with a haplotype in the same genomic region with improved yield as determined in a side-by-side comparison. This finding will have significant impact on enhancing the germplasm of glyphosate tolerant soybean. A significant portion of recent soybean breeding has utilized lines containing the Roundup Ready® trait found in event 40-3-2 (Padgette et al., 1995), with possibly as much as 80-95% of the soybean germplasm offered for sale in the United States currently containing this transgenic event. In order to continue to enhance soybean germplasm, it is desirable to be able to identify glyphosate tolerant events that also have favorable haplotype genomic regions and replace the 40-3-2 T-type genomic region in the germplasm, therefore providing elite agronomic traits of the parental line to the progeny.

In another aspect of the present invention, T-type genomic regions of insect tolerant soybean events are identified that comprise an insect resistance transgene with suitable levels of expression in linkage with a haplotype. The event GM_19459 was selected from a population of transgenic soybean events. These events contain a transgene inserted into the soybean genome that expresses a protein toxic to Lepidopteran insect pests of soybean. The various haplotype genomic regions have been mapped to assist in the selection of an event with the most favorable T-type genomic region.

In another aspect of the present invention, T-type genomic regions of insect tolerant corn events are identified that comprise an insect resistance transgene with suitable levels of expression in linkage with a haplotype. The insect tolerant corn event is selected from a population of transgenic corn events. These events contain a transgene inserted into the corn genome that expresses a protein toxic to Lepidopteran insect pests of corn. The various haplotype genomic regions are mapped to assist in the selection of an event with the most favorable T-type genomic region.

Any transgene inserted into the genome of a crop plant that can be mapped to a genomic location can then be compared to a haplotype marker developed in that location to determine if the location comprises a haplotype with an enhanced breeding value.

In one embodiment, the current invention provides genetic markers and methods for the identification and breeding of T-type genomic regions in soybean. The invention therefore allows for the first time the creation of soybean plants that combine the value of a transgene and an agronomically elite, or favorable haplotype. Favorable haplotypes are at least identified as those that have been inherited more frequently than expected in a plant population. Using the methods of the present invention, loci comprising a T-type genomic region may be introduced into potentially any desired soybean plant. Molecular markers are provided that when used in a marker assisted breeding program provide a means to identify and maintain the association of the favorable haplotype and the transgene to provide the valuable T-type genomic region. The present invention provides examples of transgenes that provide herbicide and insect resistant phenotypes to the soybean plants, other transgenes that provide stress tolerance, disease tolerance, enhanced protein, oil, amino acid or other feed quality, nutrition or processing traits are also contemplated as aspects of the present invention and germplasm comprising these T-types would be crossed to provide a stacked trait product with preferred T-type genomic regions.

In another embodiment, the current invention provides genetic markers and methods for the identification and breeding of T-type genomic regions in corn. The invention therefore allows for the first time the creation of corn plants that combine the value of a transgene and an agronomically elite, or favorable haplotype. Using the methods of the present invention, loci comprising a T-type genomic region may be introduced into potentially any desired corn plant. Molecular markers are provided that when used in a marker assisted breeding program provide a means to identify and maintain the association of the favorable haplotype and the transgene to provide the valuable T-type genomic region. The present invention provides examples of transgenes that provide an insect resistant phenotype to the corn plant, other transgenes that provide stress tolerance, herbicide tolerance, enhanced protein, oil, amino acid or other feed quality, nutrition or processing traits are also contemplated as aspects of the present invention and germplasm comprising these T-type would be crossed to provide a stacked trait product with preferred T-type genomic regions.

T-Type Genomic Region and the Concept of T-Type Value

A T-type genomic region is a novel genetic composition comprising at least one transgene, with suitable levels of expression, in genetic linkage with a haplotype. In a preferred embodiment the linkage of a transgene with a haplotype should have no observable deleterious effect on the functional integrity of the haplotype due to the local insertion of the transgene. Additionally a haplotype of a T-type genomic region could be functionally enhanced as a result of the integration into genetic linkage of a transgene. The T-type genomic region composition has the benefit of the transgene and the haplotype with which it is linked. The T-type genomic region is the genetic composition through which a transgene is diffused into germplasm by breeding.

In a preferred embodiment of the present invention, a haplotype of a T-type genomic region comprises at least two biallelic markers approximately 10 cM apart, or at least one pluriallelic locus within 5 cM of the transgene and with high polymorphic information content. Changes in a haplotype, brought about by recombination for example, may result in the modification of a haplotype so that it only comprises a portion of the original (parental) haplotype physically linked to the transgene. Any such change in a haplotype would be included in our definition of what constitutes a T-type genomic region so long as the functional integrity of the T-type genomic region is unchanged or improved. The linkage of the transgene to the haplotype or functional portion thereof that provides the desirable phenotype is preferably within about 5 cM, or within about 2 cM, or within about 1 cM of the haplotype region. The functional integrity of a haplotype is considered to be unchanged if its value is not negative with respect to yield, or is not positive with respect to maturity, or is null with respect to maturity, or amongst the best 50 percent with respect to an agronomic trait or a multiple trait index when compared to any other haplotype at the same chromosome segment in a set of germplasm (breeding germplasm, breeding population, collection of elite inbred lines, population of random mating individuals, biparental cross), or amongst the best 50 percent with respect to an agronomic trait or a multiple trait index when compared to any other haplotype across the entire genome in a set of germplasm, or the haplotype being present with a frequency of 50 percent or more in a breeding population or a set of germplasm can be taken as evidence of its high value, or any combination of these.

The benefit or value of the plant comprising in its genome a T-type genomic region is estimated by a T-value, which depends on the value of the transgene trait and the value of the haplotype to which the transgene is linked. The value of a transgene of a T-type genomic region can be estimated from the value of the trait that the transgene encodes. This value depends on the transgene trait (for example, including but not limited to: herbicide tolerance, insect resistance, disease resistance, improved nutrition, enhanced yield, improved processing trait, or stress tolerance) and could be estimated from increased crop plant output, or decrease in inputs required for crop cultivation, or any combination of these. The transgene trait also has value as a selectable or scorable marker. This has value in breeding applications to one skilled in the art because the ability to select or score for the transgene trait results in the simultaneous selection of the linked haplotype. For example in the case of a cross made with a plant comprising a T-type, wherein the transgene encodes a herbicide tolerance, spraying the progeny of that cross with the herbicide would have a high probability of selecting for the transgene and the tightly linked parental or recombinant haplotype. DNA markers that are developed to define the haplotype can be used to confirm the integrity of the T-type in the progeny of the cross.

A transgene comprising a recombinant construct may further comprise a selectable marker or scorable marker. The nucleic acid sequence serving as the selectable or scorable marker functions to produce a phenotype in cells which facilitates their identification relative to cells not containing the marker.

Examples of selectable markers include, but are not limited to, a neo or nptII gene (Potrykus et al., 1991), which codes for kanamycin resistance and can be selected for using kanamycin, G418, etc.; a bar gene which codes for bialaphos resistance; glyphosate resistant EPSP synthase, glyphosate resistant mutant EPSP synthase (Hinchee et al., 1988) which encodes glyphosate resistance, glyphosate inactivating enzymes; a nitrilase gene which confers resistance to bromoxynil (Stalker et al., 1988); a mutant acetolactate synthase gene (ALS) which confers imidazolinone or sulphonylurea resistance (European Patent Application No. 0154204); and a methotrexate resistant DHFR gene (Thillet et al., 1988).

Other exemplary scorable markers include: a β-glucuronidase or uidA gene (GUS), which encodes an enzyme for which various chromogenic substrates are known (Jefferson, 1987; Jefferson et al., 1987); an R-locus gene, which encodes a product that regulates the production of anthocyanin pigments (red color) in plant tissues (Dellaporta et al., 1988); a β-lactamase gene (Sutcliffe et al., 1978), which encodes an enzyme for which various chromogenic substrates are known (e.g., PADAC, a chromogenic cephalosporin); a luciferase gene (Ow et al., 1986); a xylE gene (Zukowsky et al., 1983) which encodes a catechol dioxygenase that can convert chromogenic catechols; an β-amylase gene (Ikatu et al., 1990); a tyrosinase gene (Katz et al., 1983), which encodes an enzyme capable of oxidizing tyrosine to DOPA and dopaquinone (which in turn condenses to melanin); and an β-galactosidase, which will turn a chromogenic β-galactose substrate.

Included within the terms "selectable or scorable markers" are also genes that encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., β-amylase, β-lactamase, phosphinothricin transferase), or proteins which are inserted or trapped in the cell wall (such as proteins which include a leader sequence such as that found in the expression unit of extension or tobacco PR-S). Other possible selectable marker genes will be apparent to those of skill in the art.

A marker is preferably GUS, green fluorescent protein (GFP), neomycin phosphotransferase II (nptII), luciferase (LUX), an antibiotic resistance gene coding sequence, or an herbicide resistance gene coding sequence. The selectable agent can be an antibiotic, for example including but not limited to, kanamycin, hygromycin, or a herbicide, for example including but not limited to, glyphosate, glufosinate, 2,4-D, and dicamba.

The T-type genomic region has a value in marker-assisted selection and marker-assisted breeding applications. Selection for a transgene and a favorable haplotype in the case where they comprise a T-type genomic region requires only one marker, whereas at least two markers would be required if the transgene and favorable haplotype are unlinked. This potential value would increase as more T-type genomic regions are accumulated or stacked together in a germplasm.

The T-value can be changed or modified by changing expression of the transgene, wherein a change is brought about at the level of transgene expression, or in the timing of transgene expression, or in the localization of transgene expression, or any combination of these. It is anticipated by this invention that the change in T-value brought by a change in any of the components of transgene expression could be effected through cis-acting (local) or trans-acting (can act at a distance not simply on the DNA molecule in which they occur) factors, or a combination of these.

Additionally, the T-value can be changed or modified by changing the haplotype with which the transgene is tightly linked. A preferred embodiment of the present invention is the improvement of the T-value by selecting or directing the transgene of an existing T-type genomic into tight linkage with a different recipient haplotype, wherein the different haplotype is associated with additional value and improved with respect to an agronomic trait or a multiple trait index over the existing T-type haplotype as determined in a side-by-side or head-to-head comparison. A change in the haplotype could also be brought about by generating or selecting for at least one recombinant T-type haplotype that is improved with respect to an agronomic trait or a multiple trait index over the existing T-type haplotype as determined in a replicated side-by-side or head-to-head comparison.

Another preferred embodiment of the present invention is to build additional value into a new or novel transgene event by selecting or directing the transgene into linkage with a recipient haplotype that has a breeding value that is not negative with respect to yield, or is not positive with respect to maturity, or is null with respect to maturity, or amongst the best 50 percent with respect to an agronomic trait or a multiple trait index when compared to any other haplotype at the same chromosome segment in a set of germplasm, or amongst the best 50 percent with respect to an agronomic trait or a multiple trait index when compared to any other haplotype across the entire genome in a set of germplasm, or alleles conferring agronomic fitness to a crop plant or the haplotype being present with a frequency of 50 percent or more in a breeding population or a set of germplasm can be taken as evidence of its high value, or any combination of these.

Another embodiment of the present invention is a selection of a plant or line for transformation with at least a first transgene, wherein the selection of the plant or line is based on it comprising in its genome a high proportion of recipient haplotypes that have a breeding value that is not negative with respect to yield, or is not positive with respect to maturity, or is null with respect to maturity, or amongst the best 50 percent with respect to an agronomic trait or a multiple trait index when compared to any other haplotype at the same chromosome segment in a set of germplasm, or amongst the best 50 percent with respect to an agronomic trait or a multiple trait index when compared to any other haplotype across the entire genome in a set of germplasm, or alleles conferring agronomic fitness to a crop plant or the haplotype being present with a frequency of 50 percent or more in a breeding population or a set of germplasm can be taken as evidence of its high value, or any combination of these.

This invention anticipates an accumulating or stacking of T-type genomic regions into plants or lines by addition of transgenes by transformation, or by crossing parent plants or lines containing different T-type genomic regions, or any combination of these. The value of the accumulated or stacked T-type genomic regions can be estimated by a composite T-value, which depends on a combination of the value of the transgene traits and the value of the haplotype(s) to which the transgenes are linked. The present invention further anticipates that the composite T-value can be improved by modifying the components of expression of one or each of the stacked transgenes. Additionally, the present invention anticipates that additional value can be built into the composite T-value by selection of at least one recipient haplotype with a favorable breeding value to which one or any of the transgenes are linked, or by selection of plants or lines for stacking transgenes by transformation or by breeding or by any combination of these.

Transgenic crops for which a method of the present invention can be applied include, but are not limited to herbicide tolerant crops, for example, Roundup Ready® Cotton 1445 and 88913; Roundup Ready® corn GA21, nk603, MON802, MON809; Roundup Ready® Sugar beet GTSB77 and H7-1; Roundup Ready® Canola RT73 and GT200; oilseed rape ZSR500, Roundup Ready® Soybean 40-3-2, MON89788-containing soybean, Roundup Ready® Bentgrass ASR368, HCN10, HCN28 and HCN92 canola, MS1 and RF1 canola, OXY-235 canola, PHY14, PHY35 and PHY36 canola, RM3-3, RM3-4 and RM3-6 chicory, A2704-12, A2704-21, A5547-35, A5547-127 soybean, GU262 soybean, W62 and W98 soybean, 19-51A cotton, 31807 and 31808 cotton, BXN cotton, FP967 flax, LLRICE06 and LLRICE62 rice, MON71800 wheat, 676 and 678 and 680 corn, B16 corn, Bt11 corn, CBH-351 corn, DAS-06275-8 corn, DBT418 corn, MS3 and MS6 corn, T14 and T25 corn, H177 corn, and TC1507 corn. Herbicides for which transgenic plant tolerance has been demonstrated and the method of the present invention can be applied, include but are not limited to: glyphosate, glufosinate, sulfonylureas, imidazolinones, bromoxynil, dalapon, dicamba, 2,4-D, cyclohezanedione, protoporphyrinogen oxidase inhibitors, and isoxaflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, U.S. Pat. No. 6,040,497 and in U.S. Pat. No. 5,094,945 for glyphosate tolerance, all of which are hereby incorporated by reference; polynucleotides encoding a glyphosate oxidoreductase, glyphosate-N-acetyl transferase, or glyphosate decarboxylase (GOX, U.S. Pat. No. 5,463,175; GAT, US Patent publications 20030083480 and 20050246798; glyphosate decarboxylase, US Patent publications 20060021093; 20060021094; 20040177399, herein incorporated by reference in their entirety); a polynucleotide molecule encoding bromoxynil nitrilase (Bxn) described in U.S. Pat. No. 4,810,648 for bromoxynil tolerance, which is hereby incorporated by reference; a polynucleotide molecule encoding phytoene desaturase (crtI) described in Misawa et al, (1993) and Misawa et al, (1994) for norflurazon tolerance; a polynucleotide molecule encoding acetohydroxyacid synthase (AHAS, aka ALS) described in Sathasiivan et al. (1990) for tolerance to sulfonylurea herbicides; and the bar gene described in DeBlock, et al. (1987) for glufosinate and bialaphos tolerance; resistant hydroxyphenyl pyruvate dehydrogenase (HPPD, U.S. Pat. No. 6,768,044). A promoter of a transgene of the present invention can express genes that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, dicamba mono-oxygenase, anthranilate synthase, glyphosate oxidoreductase, glyphosate-N-acetyl transferase, or glyphosate decarboxylase.

Transgenic crops for which the method of the present invention can be applied include, but are not limited to, insect resistant crops, for example, cotton events, such as MON15985, 281-24-236, 3006-210-23, MON531, MON757, MON1076, and COT102; or corn events, such as MIR604, BT176, BT11, CBH-351, DAS-06275-8, DBT418, MON80100, MON810, MON863, TC1507, MIR152V, 3210M, and 3243M. Insect resistant transgenic crops can provide tolerance to insect pest feeding damage and have been shown to be effective against certain Lepidopterans, and Coleopterans plant pests, and other transgenic crops that may also provide resistance to plant pests such as, certain members of Hemiptera, Homoptera, Heteroptera, Orthoptera, Thysanoptera, and plant parasitic nematodes. Disease resistant transgenic crops, for example, virus resistant papaya 55-1/63-1, and virus resistant squash CZW-3 and ZW20. Male sterility transgenic crops, for example, PHY14, PHY35 and PHY36 canola and corn events 676, 678, 680, MS3 and MS6. Additional transgenic crop plants may also provide resistance to fungal and bacterial organisms that cause plant disease.

The present invention contemplates the above listed transgenic crops and germplasm comprising the T-type genomic regions for use in breeding and stacking of T-type genomic regions, or haplotypes identified by an indirect mapping method, or any combination of these to increase T-type value or to enhance overall germplasm quality as described in the methods of the present invention.

Haplotypes

A "haplotype" is a segment of DNA in the genome of an organism that is assumed to be identical by descent for different individuals when the knowledge of identity by state at one or more loci is the same in the different individuals, and that the regional amount of linkage disequilibrium in the vicinity of that segment on the physical or genetic map is high. A haplotype can be tracked through populations and its statistical association with a given trait can be analyzed. Thus, a haplotype association study allows one to define the frequency and the type of the ancestral carrier haplotype. An "association study" is a genetic experiment where one tests the level of departure from randomness between the segregation of alleles at one or more marker loci and the value of individual phenotype for one or more traits. Association studies can be done on quantitative or categorical traits, accounting or not for population structure and/or stratification.

A haplotype analysis is important in that it increases the statistical power of an analysis involving individual biallelic markers. In a first stage of a haplotype frequency analysis, the frequency of the possible haplotypes based on various combinations of the identified biallelic markers of the invention is determined. The haplotype frequency is then compared for distinct populations and mapping population. Generally, as a result of prior germplasm improvement, the greater the haplotype frequency in a population of set of germplasm the greater its value has been to the germplasm, described as the alleles associated with agronomic fitness of a crop plant (U.S. Pat. No. 5,437,697, herein incorporated by reference in its entirety). A favorable haplotype can be selected based on its frequency in a set of germplasm, generally a frequency of 50 percent or more would indicate that the haplotype has value in the germplasm. A haplotype that occurs at a high frequency would be favorable for targeting with a transgene or selection of a T-type wherein the haplotype has a high frequency in the germplasm would be considered favorable. A haplotype occurring at any frequency in the germplasm can be correlated to a trait and the haplotype can be given a value based on a single trait or a combination of traits. A favorable haplotype will provide one or more favorable traits to a germplasm. In general, any method known in the art to test whether a trait and a genotype show a statistically significant correlation may be used. Methods for determining the statistical significance of a correlation between a phenotype and a genotype, in this case a haplotype, may be determined by any statistical test known in the art and with any accepted threshold of statistical significance being required. The application of particular methods and thresholds of significance are well with in the skill of the ordinary practitioner of the art.

In plant breeding populations, linkage disequilibrium (LD), which is the level of departure from random association between two or more loci in a population, often persists over large chromosomal segments. Although it is possible for one to be concerned with the individual effect of each gene in the segment, for a practical plant breeding purpose, what generally matters is what is the average impact the region has for the trait(s) of interest(s) when present in a line, hybrid or variety. The amount of pair-wise LD (using the $r^2$ statistics) was plotted against the distance in centiMorgans (cM, one hundredth of a Morgan, on average one recombination per meiosis, recombination is the result of the reciprocal exchange of chromatid segment between homologous chromosome paired at meiosis, and it is usually observed through the association of alleles at linked loci from different grandparents in the progeny) between the markers for a reference germplasm set, for example, a set of 791 soybean elite US lines and 1211 SNP loci with a rare allele frequency greater than 5 percent. A 200 data points moving average curve was an indicator of the presence of LD even for loci 10 cM apart. Thus when predicting average effect of chromosome segments, one should consider segments a few centiMorgans long, and this is the acception given to a haplotype region, that is a chromosome segment a few centiMorgans long that persists over multiple generations of breeding and that is carried by one or more breeding lines. This segment can be identified with multiple linked marker loci it contains, and the common haplotype identity at these loci in two lines gives a high degree of confidence of the identity by descent of the entire subjacent chromosome segment carried by these lines.

One should specify what the favorable haplotypes are and what their frequency in the germplasm is. Thus, one would obtain or generate a molecular marker survey of the germplasm under consideration for breeding and/or propagation of a transformation event. This marker survey will generate a fingerprint of each line. These markers are assumed to have their approximate genomic map position known. To simplify downstream analyses, quality assurance and missing data estimations steps may need to be implemented at this stage to produce a complete and accurate data matrix (marker genotype by line). Error detections and missing data estimations may require the use of parent-offspring tests, LD between marker loci, interval mapping, re-genotyping, etc.

Markers are then grouped based on their proximity. This grouping may be arbitrary (e.g. "start from one end of the chromosome and include all markers that are within 10 cM of the first marker included in the segment, before starting the next segment") or based on some statistical analysis (e.g. "define segment breakpoints based on LD patterns between adjacent loci").

When a large set of lines is considered, and multiple lines have the same allele at a marker locus, it is needed to ascertain whether identity by state (IBS) at the marker locus is a good predictor of identity by descent (IBD) at the chromosomal region surrounding the marker locus. "Identity by descent" (IBD) characterizes two loci/segment of DNA that are carried by two or more individuals and are all derived from the same ancestor. "Identity by state" (IBS) characterizes two loci/segments of DNA that are carried by two or more individuals and have the same alleles at the observable loci. A good indication that a number of marker loci in a segment are enough to characterize IBD for the segment is that they can predict the allele present at other marker loci within the segment.

To estimate the frequency of a haplotype, the base reference germplasm has to be defined (collection of elite inbred lines, population of random mating individuals, etc.) and a representative sample (or the all population) has to be genotyped. The haplotype frequency can then be determined by simple counting if considering a set of inbred individuals. Estimation methods that employ computing techniques like the Expectation/Maximization algorithm will be needed if individuals genotyped are heterozygous at more the one loci in the segment and linkage phase is unknown (Excoffier and Slatkin, 1995). Preferably, a method based on an expectation-maximization (EM) algorithm (Dempster et al. 1977) leading to maximum-likelihood estimates of haplotype frequencies under the assumption of Hardy-Weinberg proportions (random mating) is used (Excoffier and Slatkin, 1995). With the haplotype estimates, and the identity of each chromosome segment for each candidate host line, it is further possible to rank lines according to their probability of giving rise to events located in high value haplotypes. Several probability distributions of an event to be located in a chromosome segment could be used, according to the degree of knowledge acquired on the physical size of each segment and the random or pattern-following mode of insertion of a transgene in the genome. Alternative approaches can be employed to perform association studies: genome-wide association studies, candidate region association studies and candidate gene association studies. The biallelic markers of the present invention may be incorporated in any map of genetic markers of a plant genome in order to perform genome-wide association studies.

The present invention comprises methods to detect an association between a haplotype and a favorable property or a multiple trait index. A multiple trait index (MTI) is a numerical entity that is calculated through the combination of single trait values in a formula. Most often calculated as a linear combination of traits or normalized derivations of traits, it can also be the result of more sophisticated calculations (for example, use of ratios between traits). This MTI can then be used in genetic analysis as if it where a trait. A favorable haplotype provides a favorable property to a parent plant and to the progeny of the parent when selected by a marker means or phenotypic means. The method of the present invention provides for selection of favorable haplotypes and the accumulation of favorable haplotypes in a breeding population, for example one or more of the haplotypes identified in the present invention. A particular embodiment of the present invention, a transgene is associated with a favorable haplotype to create a T-type that is accumulated with other favorable haplotypes to enhance a germplasm.

Accumulation of T-Type Genomic Regions and Favorable Haplotypes

Another embodiment of this invention is a method for enhancing accumulation of one or more haplotypes in a germplasm. The transformation of a plant cell with a transgene means that the transgene DNA has been inserted into a genomic DNA region of the plant. Genomic regions defined as haplotype regions include genetic information and provide phenotypic traits to the plant. Variations in the genetic information result in variation of the phenotypic trait and the value of the phenotype can be measured. The genetic mapping of the haplotype regions and genetic mapping of a transgene insertion event allows for a determination of linkage of a transgene insertion with a haplotype. Any transgene that has a DNA sequence that is novel in the genome of a transformed plant can in itself serve as a genetic marker of the transgene and the genomic region in which it has inserted. For example, in the present invention, a transgene that was inserted into the genome of a soybean plant provides for the expression of a glyphosate resistant 5-enolpyruvylshikimate-3-phosphate synthase that has a DNA coding sequence comprised within SEQ ID NO:28 disclosed in U.S. Pat. No. 6,660,911 and SEQ ID NO:9 disclosed in U.S. Pat. No. 5,633,435, both herein incorporated by reference, from which a DNA primer or probe molecule can be selected to function as a genetic marker for the transgene in the genome.

Additionally, a transgene may provide a means to select for plants that have the insert and the linked haplotype region. Selection may be due to tolerance to an applied phytotoxic chemical such as a herbicide or antibiotic. Selection may be due to detection of a product of a transgene, for example, an mRNA or protein product. Selection may be conducted by detection of the transgene DNA inserted into the genome of the plant. A transgene may also provide a phenotypic selection means, such as, a morphological phenotype that is easily to observe, this could be a seed color, seed germination characteristic, seedling growth characteristic, leaf appearance, plant architecture, plant height, and flower and fruit morphology, or selection based on an agronomic phenotype, such as, yield, herbicide tolerance, disease tolerance, insect tolerance, enhance feed quality, drought tolerance, cold tolerance, or any other agronomic trait provided by a transgene.

During the development of improved crop plants by insertion of transgenic genes often hundreds of plants are produced with different transgene insertion locations. These insertion events occur throughout the genome of the plant and are incorporated into tight linkage with many different haplotype regions. The present invention provides for the screening of transgenic events that have a transgene insertion into tight linkage with favorable haplotype regions and selection of these events for use in a breeding program to enhance the accumulation of favorable haplotype regions. The method includes: a) inserting a transgene into a genome of a plant cell and regenerating the plant cell into an intact transformed plant using plant transformation and regeneration methods previously described and known in the art of plant biotechnology; and b) determining a map location of the transgene in the genome of the transformed plant using DNA markers of the transgene and linked genomic regions; and c) correlating the map location to a tightly linked haplotype, wherein the transgene and the haplotype comprises a T-type genomic region in the transformed plant; and d) crossing the transformed plant with a second plant that may also be transformed to contain at least one T-type genomic region that is different from the first transformed plant T-type genomic region or the second plant may contain a favorable haplotype region identified by genetic markers that is different from the first transformed plant; and e) selecting at least one progeny plant by detecting expression of the transgene of the first plant or selecting by the presence of a marker associated with the transgene, wherein the progeny plant comprises in its genome at least a portion of the T-type genomic region of the first plant and at least one T-type genomic region or favorable haplotype of the second plant; and f) using the progeny plant in activities related to germplasm improvement the activities selected from the group consisting of using the plant for making breeding crosses, further testing of the plant, advancement of the plant through self fertilization, use of the plant or parts thereof for transformation, use of the plant or parts thereof for mutagenesis, and use of the plant or parts thereof for TILLING (e.g. McCallum et al., 2000).

Using this method, the present invention contemplates that preferred T-type genomic regions are selected from a large population of T-type genomic regions, and the preferred T-type genomic regions have an enhanced T-value in the germplasm of a crop plant. Additionally, the preferred T-type genomic region can be used in the described breeding method to accumulate other beneficial T-type genomic regions and favorable haplotype regions and maintain these in a breeding population to enhance the overall germplasm of the crop plant. Crop plants considered for use in the method include but are not limited to, corn, soybean, cotton, wheat, rice, canola, oilseed rape, sugar beet, *sorghum*, millet, alfalfa, vegetable crops, forest trees, and fruit crops.

Genome Mapping of a T-Type Genomic Region

Another embodiment of this invention is a method for indirect mapping at least one T-type genomic region. Mapping of the T-type genomic region in the genome of a plant provides for selection of favorable haplotype regions that comprise the T-type genomic region. The present invention provides a method for mapping of the transgene insertion event and its association with a genomic region and location on a genome map of a plant. The method may include the following steps:

(a) Obtaining the DNA sequence of the genome flanking the transgene insertion event;

(b) Comparing the DNA sequence chromatogram to eliminate paralogous sequences when two or more sequences of high homology are obtained;

(c) Searching for the DNA sequence in a sequence database to verify whether the insertion event has interrupted an endogenous gene;

(d) Designing one or a plurality of pairs of DNA primer molecules on either or both the 5' and 3' genomic regions flanking the transgene insertion. When multiple pairs of primers are designed, it can be done in such a way as to obtain overlapping PCR products from each genomic flanking region to ensure substantial coverage of the associated genomic DNA;

(e) Using the parent lines of a mapping population(s) as template for PCR;

(f) Sequencing the PCR products obtained from these primers/line combinations;

(g) Identifying SNPs, or other polymorphic feature such as indels or SSRs, between the parents of at least one of the mapping populations;

(h) Repeating steps (d) through (g) on additional flanking sequence, sliding away from the site of insertion in the 5' and 3' directions, until polymorphic sites are found, or to obtain additional ones;

(i) Designing an assay to score the progeny plants of the mapping population(s);

(j) Perform a linkage analysis to ascertain the map position of these polymorphism and consequently of the location of the event;

(k) Correlate map position with the location of a haplotype region.

The genome flanking the transgene insertion event can comprise a DNA segment of from a few hundred to tens of thousands of nucleotide base pairs or a sufficient length to identify a polymorphism. The genomic flanking region can be from the 5' or 3' end of the transgene insert location extending into the genome from the insert site. The “polymerase chain reaction” (PCR) is a process of in vitro geometrical amplification of a target DNA segment through the use of a heat-resistant DNA polymerase and cyclic variation of temperature to allow for repetitive denaturing, primer annealing and amplification or template DNA. “Paralogous sequences” are two sequences of DNA with a high degree of similarity but belong to different loci on the genome. A “mapping population” is a set of individuals where alleles at marker loci and possibly at one or a plurality of Quantitative Trait Loci (QTL) are segregating, in a way that presence of linkage disequilibrium can be taken of evidence as proximity on the chromosome and there is a positive correlations between proximity and disequilibrium. The mapping population is the same plant species or a plant species demonstrating synteny or colinearity. These populations can be used to estimate the relative positions of marker loci among themselves or between these and QTLs. Generally mapping populations are segregating populations. The method can be applied to any crop species, particular important crop species are, for example, corn, soybean, cotton, wheat, rice, canola, oilseed rape, sugar beet, *sorghum*, millet, alfalfa, vegetable crops, forest trees, and fruit crops. There are maps available to one skilled in the art for one or more of these crops, by way of example, genetic maps are referenced for maize (Lee et al., 2002), soybean (Ferreira et al., 2000), cotton (Lacape et al., 2003), and canola (Cheung et al., 1997). De novo mapping populations can also be generated for any crop of interest and a genetic map crated that is useful in the present invention to map the haplotype regions in which a transgene has inserted.

Identification of cloned genomic DNA regions for example, those contained in a Bac library can be probed with DNA markers developed to identify the haplotype linked with a transgenic insertion. Additional DNA markers can be developed by sequencing the Bac clones and inspecting for polymorphisms in the sequence. Genes of interest can be isolated from the Bac clones that can be used as transgenes to improve the performance of the same crop species or different crop species.

Recombinant Vectors and Transgenes

Means for preparing recombinant vectors are well known in the art. Methods for making recombinant vectors particularly suited to plant transformation include, without limitation, those described in U.S. Pat. Nos. 4,971,908, 4,940,835, 4,769,061 and 4,757,011. These type of vectors have also been reviewed (Rodriguez et al., 1988; Glick et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaMVCN transfer control vector, have also been described (Fromm et al., 1985). Many crops species have been transformed to contain one or more transgenes of agronomic importance that in themselves provides a favorable property to the plant. One example is a transgene that confers herbicide tolerance to the crop plant. Transgenes that encode herbicide tolerance proteins that have been transformed and expressed in plants include, for example, a 5-enolpyruvylshikimate-3-phosphate synthase (EPSPS) protein conferring glyphosate resistance and proteins conferring resistance to others herbicides, such as glufosinate or bromoxynil (Comai et al., 1985; Gordon-Kamm et al., 1990; Stalker et al., 1988; Eichholtz et al., 1987; Shah et al., 1986; Charest et al., 1990). Further examples include the expression of enzymes such as dihydrofolate reductase and acetolactate synthase, mutant ALS and AHAS enzymes that confer resistance to imidazalinone or a sulfonylurea herbicides (Lee et al., 1988 and Miki et al., 1990), a phosphinothricin-acetyl-transferase conferring phosphinothricin resistance (European application No. 0 242 246), proteins conferring resistance to phenoxy proprionic acids and cycloshexones, such as sethoxydim and haloxyfop (Marshall et al., 1992); and proteins conferring resistance to triazine (psbA and gs+ genes) and benzonitrile (nitrilase encoding gene, Przibila et al. (1991).

A plant of the present invention may also comprise a transgene that confers resistance to insect, pest, viral, or bacterial attack. For example, a transgene conferring resistance to a pest, such as soybean cyst nematode was described in PCT Application WO96/30517 and PCT Application WO93/19181. Jones et al. (1994) describe cloning of the tomato Cf-9 gene for resistance to *Cladosporium falvum*); Martin et al. (1993) describe a tomato Pto gene for resistance to *Pseudomonas syringae* pv. and Mindrinos et al. (1994) describe an *Arabidopsis* RSP2 gene for resistance to *Pseudomonas syringae*. *Bacillus thuringiensis* endotoxins may also be used for insect resistance, for example, Geiser et al. (1986).

The expression of viral coat proteins as transgenes in transformed plant cells is known to impart resistance to viral infection and/or disease development affected by the virus from which the coat protein gene is derived, as well as by related viruses (Beachy et al., 1990).

Transgenes may also be used conferring increased nutritional value or another value-added trait. One example is modified fatty acid metabolism, for example, by transforming a plant with an antisense gene of stearoyl-ACP desaturase to increase stearic acid content of the plant, (Knutzon et al., 1992). A sense desaturase gene may also be introduced to alter fatty acid content. Phytate content may be modified by introduction of a phytase-encoding gene to enhance breakdown of phytate, adding more free phosphate to the transformed plant. Modified carbohydrate composition may also be affected, for example, by transforming plants with a gene coding for an enzyme that alters the branching pattern of starch (Shiroza et al., 1988, nucleotide sequence of *Streptococcus mutants* fructosyltransferase gene); Steinmetz et al. (1985) (nucleotide sequence of *Bacillus subtilis* levansucrase gene); Pen et al. (1992), production of transgenic plants that express *Bacillus lichenifonnis* α-amylase); Elliot et al. (1993), nucleotide sequences of tomato invertase genes); Søgaard et al. (1993), site-directed mutagenesis of barley α-amylase gene; and Fisher et al. (1993), maize endosperm starch branching enzyme II.

Transgenes may also be used to alter protein metabolism. For example, U.S. Pat. No. 5,545,545 describes lysine-insensitive maize dihydrodipicolinic acid synthase (DHPS), which is substantially resistant to concentrations of L-lysine which otherwise inhibit the activity of native DHPS. Similarly, EP 0640141 describes sequences encoding lysine-insensitive aspartokinase (AK) capable of causing a higher than normal production of threonine, as well as a subfragment encoding antisense lysine ketoglutarate reductase for increasing lysine.

A transgene may be employed that alters plant carbohydrate metabolism. For example, fructokinase genes are known for use in metabolic engineering of fructokinase gene expression in transgenic plants and their fruit (U.S. Pat. No. 6,031,154). Further examples of transgenes that may be used are genes that alter grain yield. For example, U.S. Pat. No. 6,486,383 describes modification of starch content in plants with subunit proteins of adenosine diphosphoglucose pyrophosphorylase ("ADPG PPase"). In EP0797673, transgenic plants are discussed in which the introduction and expression of particular DNA molecules results in the formation of easily mobilized phosphate pools outside the vacuole and an enhanced biomass production and/or altered flowering behavior. Still further known are genes for altering plant maturity. U.S. Pat. No. 6,774,284 describes DNA encoding a plant lipase and methods of use thereof for controlling senescence in plants. U.S. Pat. No. 6,140,085 provides FCA genes for altering flowering characteristics, particularly timing of flowering. U.S. Pat. No. 5,637,785 discusses genetically modified plants having modulated flower development such as having early floral meristem development and comprising a structural gene encoding the LEAFY protein in its genome.

Genes for altering plant morphological characteristics are also known and may be used in accordance with the invention. U.S. Pat. No. 6,184,440 discusses genetically engineered plants which display altered structure or morphology as a result of expressing a cell wall modulation transgene. Examples of cell wall modulation transgenes include a cellulose binding domain, a cellulose binding protein, or a cell wall modifying protein or enzyme such as endoxyloglucan transferase, xyloglucan endo-transglycosylase, an expansin, cellulose synthase, or a novel isolated endo-1,4-β-glucanase.

A transgene that provides a favorable property can be associated with plant morphology, physiology, growth and development, yield, nutritional enhancement, disease or pest resistance, or environmental or chemical tolerance. A transgene that provides a beneficial agronomic trait to crop plants may be, for example, include but is not limited to the following examples of genetic elements comprising herbicide resistance (U.S. Pat. No. 5,633,435 and U.S. Pat. No. 5,463,175), increased yield (U.S. Pat. No. 5,716,837), insect control (U.S. Pat. No. 6,063,597; U.S. Pat. No. 6,063,756; U.S. Pat. No. 6,093,695; U.S. Pat. No. 5,942,664; and U.S. Pat. No. 6,110,464), fungal disease resistance (U.S. Pat. No. 5,516,671; U.S. Pat. No. 5,773,696; U.S. Pat. No. 6,121,436; U.S. Pat. No. 6,316,407, and U.S. Pat. No. 6,506,962), virus resistance (U.S. Pat. No. 5,304,730 and U.S. Pat. No. 6,013,864), nematode resistance (U.S. Pat. No. 6,228,992), bacterial disease resistance (U.S. Pat. No. 5,516,671), starch production (U.S. Pat. No. 5,750,876 and U.S. Pat. No. 6,476,295), modified oils production (U.S. Pat. No. 6,444,876), high oil production (U.S. Pat. No. 5,608,149 and U.S. Pat. No. 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. No. 5,985,605 and U.S. Pat. No. 6,171,640), biopolymers (U.S. Pat. No. 5,958,745 and U.S. Patent Publication US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements, methods, and transgenes described in the patents listed above are hereby incorporated by reference.

Alternatively, a transcribable polynucleotide molecule can effect the above mentioned plant characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Certain RNA molecules can also be expressed in plant cells that inhibit targets in organisms other than plants, for example, insects that feed on the plant cells and ingest the inhibitory RNA, or nematodes that feed on plant cells and ingest the inhibitory RNA. Thus, any transcribable polynucleotide molecule that encodes a transcribed RNA molecule that affects a phenotype or morphology change of interest may be useful for the practice of the present invention.

Breeding and Markers

Breeding techniques take advantage of a plant's method of pollination. There are two general methods of pollination: self-pollination, which occurs if pollen from one flower is transferred to the same or another flower of the same plant, and cross-pollination, which occurs if pollen comes to it from a flower on a different plant. Plants that have been self-pollinated and selected for type over many generations become homozygous at almost all gene loci and produce a uniform population of true breeding progeny, homozygous plants.

In development of suitable varieties, pedigree breeding may be used. The pedigree breeding method for specific traits involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and are again advanced in each successive generation. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. A selfed generation (S) may be considered to be a type of filial generation (F) and may be named F as such. After at least five generations, the inbred plant is considered genetically pure.

Each breeding program should include a periodic, objective evaluation of the efficiency of the breeding procedure. Evaluation criteria vary depending on the goal and objectives. Promising advanced breeding lines are thoroughly tested and compared to appropriate standards in environments representative of the commercial target area(s) for generally three or more years. Identification of individuals that are genetically superior because genotypic value can be masked by confounding plant traits or environmental factors. One method of identifying a superior plant is to observe its performance relative to other experimental plants and to one or more widely grown standard varieties. Single observations can be inconclusive, while replicated observations provide a better estimate of genetic worth.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Descriptions of other breeding methods that are commonly used for different traits and crops can be found in one of several reference books (Allard, 1960; Simmonds, 1979; Sneep and Hendriksen, 1979; Fehr, 1987; Fehr, 1987).

The effectiveness of selecting for genotypes with enhanced traits of interest (for example, a favorable property such as yield of a harvested plant product, for example yield of a grain, seed, fruit, fiber, forage; or an agronomic trait, for example, pest resistance such as disease resistance, insect resistance, nematode resistance, or improved growth rate, and stress tolerance; or an improved processed product of the plant, for example, fatty acid profile, amino acid profile, nutritional content, fiber quality) in a breeding program will depend upon: 1) the extent to which the variability in the traits of interest of individual plants in a population is the result of genetic factors and is thus transmitted to the progenies of the selected genotypes; and 2) how much the variability in the traits of interest among the plants is due to the environment in which the different genotypes are growing. The inheritance of traits ranges from control by one major gene whose expression is not influenced by the environment (i.e., qualitative characters) to control by many genes whose effects are greatly influenced by the environment (i.e., quantitative characters). Breeding for quantitative traits such as yield is further characterized by the fact that: 1) the differences resulting from the effect of each gene are small, making it difficult or impossible to identify them individually; 2) the number of genes contributing to a character is large, so that distinct segregation ratios are seldom, if ever, obtained; and 3) the effects of the genes may be expressed in different ways based on environmental variation. Therefore, the accurate identification of transgressive segregates or superior genotypes with the traits of interest is extremely difficult and its success is dependent on the plant breeder's ability to minimize the environmental variation affecting the expression of the quantitative character in the population.

The likelihood of identifying a transgressive segregant is greatly reduced as the number of traits combined into one genotype is increased. Consequently, all the breeder can generally hope for is to obtain a favorable assortment of genes for the first complex character combined with a favorable assortment of genes for the second character into one genotype in addition to a selected gene.

Introgression of a particular genomic region in a set of genomic regions that contain a transgene, or transgenes into a plant germplasm is defined as the result of the process of backcross conversion. A plant germplasm into which a novel DNA sequence has been introgressed may be referred to as a backcross converted genotype, line, inbred, or hybrid. Additionally, an introgression of a particular genomic region or transgene may be conducted by a forward breeding process. Similarly a plant genotype lacking the desired DNA sequence may be referred to as an unconverted genotype, line, inbred, or hybrid. During breeding, the genetic markers linked to a T-type genomic region may be used to assist in breeding for the purpose of producing soybean plants with increased yield and a transgenic trait. Backcrossing and marker-assisted selection, or forward breeding and marker-assisted selection in particular can be used with the present invention to introduce the T-type genomic region into any variety by conversion of that variety.

In another embodiment of this invention marker sequences are provided that are genetically linked and can be used to follow the selection of the soybean or corn haplotypes. Genomic libraries from multiple corn or soybean lines are made by isolating genomic DNA from different corn or soybean lines by Plant DNAzol Reagent" from Life Technologies now Invitrogen (Invitrogen Life Technologies, Carlsbad, Calif.). Genomic DNA are digested with Pst 1 endonuclease restriction enzyme, size-fractionated over 1 percent agarose gel and ligated in plasmid vector for sequencing by standard molecular biology techniques as described in Sambrook et al. These libraries are sequenced by standard procedures on ABI Prism®377 DNA Sequencer using commercially available reagents (Applied Biosystems, Foster City, Calif.). All sequences are assembles to identify non-redundant sequences by Pangea Clustering and Alignment Tools that is available from DoubleTwist Inc., Oakland, Calif. Sequence from multiple corn or soybean lines are assembled into loci having one or more polymorphisms, such as SNPs and/or Indels. Candidate polymorphisms are qualified by the following parameters:

(a) The minimum length of a contig or singleton for a consensus alignment is 200 bases.
(b) The percentage identity of observed bases in a region of 15 bases on each side of a candidate SNP is at least 75 percent.
(c) The minimum Phred quality in each contig at a polymorphism site is 35.
(d) The minimum Phred quality in a region of 15 bases on each side of the polymorphism site is 20.

Read data from automated sequencers varies significantly in quality due to the nature of nucleotides in a polynucleotide molecule and number of other reasons (Ewing et al., 1998). Many algorithms were developed to address the issue of accurate base pair calling (Giddings et al., 1993; Berno, 1996; Lawrence and Solovyev, 1994). The most widely used algorithm calculates the quality of the sequence as "q" in equation $q=-10\times\log 10(p)$, where p is the estimated error probability of that base call (Ewing and Green, 1998). Thus a base call having a probability of 1/1000 of being incorrect in a particular sequence is assigned a quality score of 30. Quality scores are also referred as "Phred Scores".

Selection of Plants using Marker-Assisted Selection

A primary motivation for development of molecular markers in crop species is the potential for increased efficiency in plant breeding through marker-assisted selection (MAS). Genetic marker alleles (an "allele" is an alternative sequence at a locus) are used to identify plants that contain a desired genotype at multiple loci, and that are expected to transfer the desired genotype, along with a desired phenotype to their progeny. Genetic marker alleles can be used to identify plants that contain desired genotype at one marker locus, several loci, or a haplotype, and that would be expected to transfer the desired genotype, along with a desired phenotype to their progeny.

Marker-assisted selection comprises the mapping of phenotypic traits and relies on the ability to detect genetic differences between individuals. A "genetic map" is the representation of the relative position of characterized loci (DNA markers or any other locus for which allele can be identified) along the chromosomes. The measure of distance is relative to the frequency of crossovers event between sister chromatids at meiosis. The genetic differences, or "genetic markers" are then correlated with phenotypic variations using statistical methods. In a preferred case, a single gene encoding a protein responsible for a phenotypic trait is detectable directly by a mutation which results in the variation in phenotype. More commonly, multiple genetic loci each contribute to the observed phenotype.

The presence and/or absence of a particular genetic marker allele in the genome of a plant exhibiting a favorable phenotypic trait is made by any method listed above using markers, for example, DNA markers are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. If the nucleic acids from the plant are positive for a desired genetic marker, the plant can be selfed to create a true breeding line with the same genotype, or it can be crossed with a plant with the same marker or with other desired characteristics to create a sexually crossed hybrid generation. Methods of marker-assisted selection (MAS) using a variety of genetic markers are provided. Plants selected by MAS using the methods are provided.

Marker-assisted introgression involves the transfer of a chromosome region defined by one or more markers from one germplasm to a second germplasm. The initial step in that process is the localization of the genomic region or transgene by gene mapping, which is the process of determining the position of a gene or genomic region relative to other genes and genetic markers through linkage analysis. The basic principle for linkage mapping is that the closer together two genes are on a chromosome, then the more likely they are to be inherited together. Briefly, a cross is generally made between two genetically compatible but divergent parents relative to traits under study. Genetic markers can then be used to follow the segregation of traits under study in the progeny from the cross, often a backcross (BC1), $F_2$, or recombinant inbred population.

The selection of a suitable recurrent parent is an important step for a successful backcrossing procedure. The goal of a backcross protocol is to alter or substitute a trait or characteristic in the original inbred. To accomplish this, one or more loci of the recurrent inbred is modified or substituted with the desired gene from the nonrecurrent (donor) parent, while retaining essentially all of the rest of the desired genetic, and therefore the desired physiological and morphological, constitution of the original inbred. The choice of the particular donor parent will depend on the purpose of the backcross. The exact backcrossing protocol will depend on the characteristic or trait being altered to determine an appropriate testing protocol. It may be necessary to introduce a test of the progeny to determine if the desired characteristic has been successfully transferred. In the case of the present invention, one may test the progeny lines generated during the backcrossing program as well as using the marker system described herein to select lines based upon markers rather than visual traits, the markers are indicative of the preferred T-type genomic region or a genomic region comprising a favorable haplotype.

Transformed Plants and Plant Cells

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a polynucleotide molecule of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. No. 5,015,580; U.S. Pat. No. 5,550,318; U.S. Pat. No. 5,538,880; U.S. Pat. No. 6,160,208; U.S. Pat. No. 6,399,861; and U.S. Pat. No. 6,403,865; *Agrobacterium*-mediated transformation as illustrated in U.S. Pat. No. 5,824,877; U.S. Pat. No. 5,591,616; U.S. Pat. No. 5,981,840; and U.S. Pat. No. 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), alfalfa (*Medicago sativa*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including *indica* and *japonica* varieties); *sorghum* (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); and wheat (*Triticum aestivum*). It is apparent to those of skill in the art that a number of transformation methodologies can be used and modified for production of stable transgenic plants from any number of target crops of interest. Methods for introducing a transgene are well known in the art and include biological and physical, plant transformation protocols. See, for example, Miki et al. (1993). Once a transgene is introduced into a variety it may readily be transferred by crossing. By using backcrossing, essentially all of the desired morphological and physiological characteristics of a variety are recovered in addition to the locus transferred into the variety via the backcrossing technique. Backcrossing and forward breeding methods can be used with the present invention to improve or introduce a characteristic into a plant (Poehlman and Sleper, 1995; Fehr, 1987a, b; Sprague and Dudley, 1988).

Site-Specific Integration of Transgenes

A number of site-specific recombination-mediated methods have been developed for incorporating transgene into plant genomes, as well as for deleting unwanted genetic elements from plant and animal cells. For example, the cre-lox recombination system of bacteriophage P1, described by Abremski et al. (1983); Sternberg et al. (1981) and others, has been used to promote recombination in a variety of cell types. The cre-lox system utilizes the cre recombinase isolated from bacteriophage P1 in conjunction with the DNA sequences (termed lox sites) it recognizes. This recombination system has been effective for achieving recombination in plant cells (U.S. Pat. No. 5,658,772), animal cells (U.S. Pat. No. 4,959,317 and U.S. Pat. No. 5,801,030), and in viral vectors (Hardy et al., 1997). Targeting and control of insertion or removal of transgene sequences in a plant genome can be achieved by the use of molecular recombination method (U.S. Pat. No. 6,573,425). An introduced polynucleotide molecule comprising a heterologous recombination site incorporated into a haplotype region is within the scope of the prevent invention.

Wahl et al. (U.S. Pat. No. 5,654,182) used the site-specific FLP recombinase system of *Saccharomyces cerevisiae* to delete DNA sequences in eukaryotic cells. The deletions were designed to accomplish either inactivation of a gene or activation of a gene by bringing desired DNA fragments into association with one another. Activity of the FLP recombinase in plants has been demonstrated (Lyznik et al, 1996; Luo et al., 2000).

Others have used transposons, or mobile genetic elements that transpose when a transposase gene is present in the same genome, to separate target genes from ancillary sequences. Yoder et al. (U.S. Pat. No. 5,482,852 and U.S. Pat. No. 5,792,924, both of which are incorporated herein by reference) used constructs containing the sequence of the transposase enzyme and the transposase recognition sequences to provide a method for genetically altering plants that contain a desired gene free of vector and/or marker sequences. Other methods that use DNA sequence directed bacteriophage recombinase or transposases to target specific regions are described in US 20020132350 and EP 1308516 (both of which are incorporated herein by reference). Zinc finger endonucleases can be specifically designed to recognize a DNA sequence and can target specific DNA sequences in a genome to create a recombination site useful for the insertion of a transgene (Wright et al., 2005; U.S. Pat. No. 7,030,215; US 20050208489; US 20050064474, herein incorporated by reference in their entirety), for example, targeted to a haplotype comprising the DNA sequences listed in the sequence listing of the present invention and contained in the genome of a corn or soybean plant is contemplated by the inventors.

A transgene that contains additional recombination sites when it is a component of a preferred T-type genomic region provides an opportunity to add additional transgenes to the T-type genomic region, thereby increasing the value of the region in a germplasm. The present invention contemplates that the T-type genomic region is also a site for specific recombination activities to remove or add new genetic material to the genomic region.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Haplotypes

This example illustrates identifying soybean haplotypes useful in databases for practicing the methods of this invention. The chromosomes of soybean were divided into haplotypes by following the hereditability of a large set of makers. Allelic forms of the haplotypes were identified for a set of 4 haplotypes which are listed in Table 1. With reference to Table 1, a haplotype mapped to a genomic location is identified by reference, for example C8W6H5 refers to chromosome 8, window 6 in that chromosome and haplotype 5 in that window (genomic region); SEQ_ID provides reference to the sequence listing and the marker ID number is an arbitrary identifying name for a DNA amplicon associated with the a marker locus; START_POS refers to the start position of the marker in the DNA amplicon; HAP allele refers to the nucleotide of an SNP/Indel marker at the Start position where * indicates a deletion of an Indel; "other marker states" identifies another nucleotide allele of markers in the window.

TABLE 1

Summary information of marker loci used to characterize four soybean haplotypes associated with the glyphosate tolerant soybean events, including the sequence identification (SEQ ID and marker ID number) and the position of the polymorphism (START POS) being used to characterize alleles (HAP ALLELE) in these sequences.

| Haplotype | SEQ_ID | | START POS | HAP ALLELE | Other marker states |
|---|---|---|---|---|---|
| C8W6H5 | 1 | 962360 | 277 | * | G |
| | 2 | 1324623 | 785 | A | T |
| | 3 | 1271382 | 239 | A | G |
| C16W8H43 | 4 | 1271562 | 351 | A | G |
| | 5 | 894632 | 193 | G | C |
| | 6 | 928368 | 320 | A | G |
| | 7 | 1267271 | 563 | C | A |
| | 8 | 1271614 | 126 | A | G |
| | 9 | 1271496 | 359 | T | G |
| C18W3H8 | 10 | 1271924 | 603 | G | A |
| | 11 | 1267375 | 741 | T | C |
| | 12 | 860401 | 372 | G | C |
| C19W3H6 | 13 | 1271355 | 283 | T | C |
| | 14 | 1271476 | 546 | A | C |
| | 15 | 825651 | 294 | T | C |

Example 2

Preparation of a Database with Agronomic Traits and Haplotypes

This example illustrates the preparation of a database useful in a method of this invention. With reference to Table 2 the database comprises computed values of agronomic traits, for example, yield, maturity, plant height, and lodging, for the specific allelic soybean haplotypes and the haplotype frequency in a set of breeding lines. Other traits can be measured, for example, yield of a grain, seed, fruit, fiber, forage, oil; or an agronomic trait, for example, pest resistance such as disease resistance, insect resistance, nematode resistance, or improved growth rate, and stress tolerance; or an improved processed product of the plant, for example, fatty acid profile, amino acid profile, nutritional content, fiber quality and a database compiled for the values of each haplotype for these other traits. The agronomic trait values of these haplotypes represent the predicted population change in mean value for the trait listed if the haplotype was fixed in the germplasm, everything else staying the same. The values for "yield" are in bushels of soybeans per acre. The values for "maturity" are in days (maturity of a soybean line is the relative flowering time of that line compared to a set of standard checks of defined maturity). The values for "plant height" are in inches of height measured from the soil surface to the tip of the uppermost plant tissue at maturity. The values of "lodging" are a percent of plants compared to a set of standard checks (lodging is a phenomenon in which the main stem of crop plants has moved from the vertical by a large angle, sometimes to the point of the plants being laying on the ground).

The breeding values for each of the haplotypes are used to select the haplotype that in combination with a transgene will be the most beneficial for the improvement of the germplasm of the crop. The breeding value is a combination of measured traits and the estimation of how these traits will affect germplasm improvement. The soybean haplotypes associated with the transgenic events for glyphosate tolerance were measured and the results shown in Table 2. The Haplotype C8W6H5 would be a favorable haplotype for its effect on yield, and haplotype C18W3H8 would be a favorable haplotype for its very high frequency in the germplasm (94 percent), indicating that little variability is present in the target soy germplasm for this chromosome segment, making the diffusion process of a transgenic event in it neutral. Haplotype C19W3H6 is generally neutral with respect to yield.

TABLE 2

The calculated breeding values of four haplotypes described for yield, maturity, plant height, and lodging. The frequency of the haplotype in the soybean germplasm was estimated from a sample of 365 soybean lines.

| Haplotype | Yield (Bushels/acre) | Maturity (Days) | Plant height (inches) | Lodging (%) | Frequency in a breeding population |
|---|---|---|---|---|---|
| C8W6H5 | 1.689 | 0.989 | −0.195 | −0.027 | 21% |
| C16W8H43 | −0.447 | −0.211 | −0.514 | −0.101 | 42% |
| C18W3H8 | 0.000 | 0.000 | 0.000 | 0.000 | 94% |
| C19W3H6 | −0.071 | 0.232 | −0.495 | 0.001 | 58% |

The haplotype regions were determined for each of the four new glyphosate tolerant soybean events. 17194 is linked to haplotype C16W8H43, 17426 is linked to haplotype C18W3H8, 19703 is linked to haplotype C19W3H6, and 19788 is linked to haplotype C8W6H5. The relative effect of these haplotypes was measured as illustrated in Table 2. This represents the predicted population change in mean value for the trait listed if the haplotype was fixed in the germplasm, everything else staying the same. The T-type of 19788 and the associated C8W6H5 haplotype is the most favorable of the four T-types that were measured. This result demonstrates that it is important in a process to improve crop performance through transgenic methods that both transgenic events and the linked haplotype regions are evaluated to continue to enhance crop productivity.

The new glyphosate tolerant events were compared in replicated field trials to a backcross conversion of 40-3-2 into A3244 germplasm. This was demonstrated in replicated field trials including yield data collected from seventeen locations in the United States. The A3244 (U.S. Pat. No. 5,659,114, ATCC number 97549) is an elite soybean germplasm from Asgrow (Monsanto, St Louis, Mo.) that was used as the parent line for transformation to generate the new glyphosate tolerant soybean events 17194, 17426, 19703, and 19788. The results of the yield study showed that 40-3-2 A3244 backcross yielded an average of 60.7 bu/acre, 19788 an average of 65.6 bu/acre, 19703 an average of 65.7 bu/acre, 17426 an average of 65.3 bu/acre, and 17194 an average of 65.8 bu/acre. The four new lines have an approximate yield advantage of 5 bu/acre over the same genotype with the introgressed 40-3-2 T-type genomic region. When the haplotype of each is considered then the most favorable event is 19788.

These analyses demonstrate the value of determining the T-type for each transgenic event that is being developed as a commercial product. Failure to consider the agronomic effects of the haplotype region in which the transgene has introgressed can result in the introduction of a low performing event into the germplasm of a crop.

Example 3

Use of Breeding Values

The haplotype regions and breeding values of each were determined for four haplotype regions in which an insect tolerance gene was inserted into the genome of a soybean plant. The relative breeding value for each haplotype regions is shown in Table 3, the definitions of the measurements are the same as described in Example 2. The table is a database for determining the haplotype and its breeding value in which an insect tolerance gene was inserted (a T-type). A transgenic event comprising the T-type is selected using the database information. A particular event, GM_19459, contains the T-type of the insect tolerance gene associated with C6W4H1 haplotype that is a favorable haplotype for maturity.

TABLE 3

The calculated breeding values for yield, maturity, plant height, and lodging of four haplotypes for the insect tolerant soybean events. The frequency of the haplotype in the germplasm was estimated from 2589 soybean lines.

| Haplotype | Yield (Bushels/acre) | Maturity (Days) | Plant height (inches) | Lodging (%) | Haplotype frequency |
|---|---|---|---|---|---|
| C1W1H2 | 0.075 | 0.244 | 0.057 | 0.018 | 16% |
| C1W2H1 | 0.160 | 0.314 | 0.069 | 0.022 | 67% |
| C14W7H2 | 0.130 | 0.648 | −0.101 | −0.069 | 62% |
| C6W4H1 | −0.156 | −0.111 | — | 0.070 | 29% |

Allelic forms of the haplotypes were identified for a set of 4 haplotypes associated with transgenic insect resistant soybeans as listed in Table 4. With reference to Table 4, a haplotype mapped to a genomic location is identified by reference, for example C1W1H2 refers to chromosome 1, window 1 in that chromosome and haplotype 2 in that window (genomic region); SEQ_ID provides reference to the sequence listing and the marker ID number is an arbitrary identifying name for a DNA amplicon associated with the a marker locus; START_POS refers to the start position of the marker in the DNA amplicon; HAP allele refers to the nucleotide of an SNP/Indel marker at the Start position where * indicates a deletion of an Indel; "other marker states" identifies another nucleotide allele of markers in the window; "NA" indicated another marker allele is not present.

TABLE 4

Summary information of marker loci used to characterize four soybean haplotypes associated with the insect tolerant soybean events, including the sequence identification (SEQ ID and marker ID number) and the position of the polymorphism (START POS) being used to characterize alleles (HAP ALLELE) in these sequences.

| Haplotype | | SEQ_ID | START POS | HAP ALLELE | Other marker states |
|---|---|---|---|---|---|
| C1W1H2 | 16 | NS0092678 | 0 | C | T |
| | 17 | NS0092617 | 0.4 | A | G |
| | 18 | NS0101549 | 1.4 | A | G |
| | 19 | NS0127917 | 1.4 | C | A |
| | 20 | NS0120003 | 1.8 | A | T |
| | 21 | NS0118494 | 3 | C | T |
| C1W2H1 | 22 | NS0124158 | 3 | A | G |
| | 23 | NS0101025 | 11.3 | C | T |
| | 24 | NS0101038 | 11.3 | A | C |
| | 25 | NS0127234 | 11.3 | T | G |
| | 26 | NS0129173 | 11.3 | T | A |
| | 27 | NS0097228 | 16.2 | C | NA |
| C14W7H2 | 28 | NS0096079 | 68.5 | T | C |
| C6W4H1 | 29 | NS0125775 | 30.3 | G | C |
| | 30 | NS0130788 | 30.3 | T | C |
| | 31 | NS0093984 | 32.9 | C | T |
| | 32 | NS0096925 | 32.9 | A | * |

Example 4

Application to Corn Breeding

This example illustrates the haplotype regions and breeding values that were determined for four haplotype regions in which an insect tolerance gene was inserted into the genome of a corn plant (LH172). The relative breeding value for each haplotype regions is shown in Table 5, the definitions of the measurements are the same as described in Example 2. The table is a database for determining the haplotype and its breeding value in which an insect tolerance gene was inserted (a T-type). A transgenic event comprising the T-type is selected using the database information. A particular event contains the T-type of the insect tolerance gene associated with the C1W36H2 haplotype.

TABLE 5

Calculated breeding value for yield of four haplotypes for insect tolerant corn events. The frequency of the haplotype in the germplasm was estimated from 6335 corn lines.

| Haplotype | Yield (Bushels/acre) | Haplotype frequency |
|---|---|---|
| C1W19H14 | 0.168 | 9.2% |
| C1W30H4 | −0.781 | 3.3% |
| C1W36H2 | 0.008 | 18% |
| C8W4H5 | 0.377 | 15% |

Allelic forms of the haplotypes were identified for a set of 4 haplotypes for the transgenic insect resistant corn as listed in Table 6. With reference to Table 6, a haplotype mapped to a genomic location is identified by reference, for example C1W19H14 refers to chromosome 1, window 19 in that chromosome and haplotype 14 in that window (genomic region); SEQ_ID provides reference to the sequence listing and the marker ID number is an arbitrary identifying name for a DNA amplicon associated with the a marker locus; START_POS refers to the start position of the marker in the DNA amplicon; HAP allele refers to the nucleotide of an SNP/Indel marker at the Start position where * indicates a deletion of an Indel; "other marker states" identifies another nucleotide allele of markers in the window.

TABLE 6

Summary information of marker loci used to characterize four corn haplotypes associated with the insect tolerant corn events, including the sequence id (SEQ ID and marker ID number) and the position of the polymorphism (START POS) being used to characterize alleles (HAP ALLELE) in these sequences.

| Haplotype | | SEQ_ID | START POS | HAP ALLELE | Other marker states |
|---|---|---|---|---|---|
| C1W19H14 | 33 | NC0053983 | 109.4 | T | C |
| | 34 | NC0113263 | 110.1 | A | G |
| | 35 | NC0008901 | 110.8 | T | C |
| | 36 | NC0143254 | 110.9 | A | G |
| | 37 | NC0030198 | 111 | A | G |
| | 38 | NC0080733 | 111 | T | G |
| | 39 | NC0104474 | 111 | C | T |
| | 40 | NC0033728 | 113.3 | C | A |
| C1W30H4 | 41 | NC0029506 | 113.6 | C | G |
| | 42 | NC0039502 | 195.5 | G | A |
| | 43 | NC0111626 | 196.4 | T | C |
| | 44 | NC0008982 | 198.4 | A | G |
| | 45 | NC0040427 | 199.4 | G | T |
| | 46 | NC0033427 | 199.8 | G | T |
| C1W36H2 | 47 | NC0148362 | 200 | G | A |
| | 48 | NC0146570 | 237 | T | G |
| | 49 | NC0008996 | 238.1 | A | T |

TABLE 6-continued

Summary information of marker loci used to characterize four corn haplotypes associated with the insect tolerant corn events, including the sequence id (SEQ ID and marker ID number) and the position of the polymorphism (START POS) being used to characterize alleles (HAP ALLELE) in these sequences.

| Haplotype | | SEQ_ID | START POS | HAP ALLELE | Other marker states |
|---|---|---|---|---|---|
| C8W4H5 | 50 | NC0013490 | 240.7 | T | C |
| | 51 | NC0111628 | 57.3 | A | G |
| | 52 | NC0026720 | 58.7 | A | C |
| | 53 | NC0037392 | 60 | C | T |
| | 54 | NC0027485 | 60.1 | C | T |

Example 5

Indirect Mapping of a T-Type Genomic Region

DNA markers are identified in the genomic region flanking a transgene insert to provide a means to identify the genomic location of the transgene by comparison of the DNA markers to a mapping population. DNA markers can be developed to any transgenic event by isolation of the genomic region, sequencing of the region, isolation of the same region in a mapping population of the crop plant, and determining the location relative to markers known in the mapping population. The association of the transgene with mapped phenotypes, quantitative trait loci comprising a haplotype genomic region can be determined.

For example, for MON89788 a DNA primer pair was selected from a DNA sequence that extends into the genome 5' to the transgene insertion site (SEQ ID NO:55 and 56) and into the 3' genomic region relative to the transgene insertion site (SEQ ID NO:57-58). A DNA amplification method was used to produce DNA products that comprise a portion of the soybean genome from the 5' and 3' regions of the transgene insertion site. These DNA products were sequenced. The same primer pairs were used to amplify DNA from seven soybean lines (507354, Minsoy, Noir, HS1, PIC, 88788, A3244) that are parents of four mapping populations. A single nucleotide polymorphism (SNP) was identified at position 119 (SNP119, SEQ ID NO:59) from the 3' flanking sequences when comparing sequences across different lines. Table 7 shows the allelic composition at this position on eight lines tested.

TABLE 7

Polymorphism at flanking sequences in different soybean lines comprising MON89788.

| | 5' Flanking | 3' Flanking |
|---|---|---|
| Position | 2809 | 119 |
| 507354 | A | T |
| Minsoy | A | T |
| Noir | A | T |
| HS1 | A | T |
| PIC | T | C |
| 88788 | | T |
| A3244 | | T |
| 507355 | A | T |

A Taqman® (PE Applied Biosystems, Foster City, Calif.) end point assay was developed from SNP119 in accordance to instructions provided by the manufacturer. Primer and probe sequences are given in Table 8. To map the SNP119 polymophism, an F2 population, derived from a cross between HS1×PI407305 (PIC), consisting of 140 individuals, was used. Map position of SNP119 was determined by placing the allelic scores against the existing allelic data set using MapMaker (Lincoln and Lander, 1990). SNP119 was found on linkage group D1a+Q (Song, Q. J., et al., 2004). Thus, MON89788 was indirectly mapped to this same position.

TABLE 8

Primer and probe molecules for Taqman assay for mapping haplotype

| | | |
|---|---|---|
| Forward Primer SEQ ID NO: 60 | 19788_3E-119F | CGTTCTCGACTTCAACCATATGTGA |
| Reverse Primer SEQ ID NO: 61 | 19788_3E-119R | GCATGGAATAAAGCGGAAAGGAAAG |
| VIC Probe SEQ ID NO: 62 | 19788_3E-119V2 | CCATGGTATCATAGGCA |
| Fam Probe SEQ ID NO: 63 | 19788_3E-119M2 | CCATGGTATCGTAGGCA |

A deposit of Monsanto Technology LLC, soybean seed comprising event MON89788 disclosed above and recited in the claims, has been made under the Budapest Treaty with the American Type Culture Collection (ATCC), 10801 University Boulevard, Manassas, Va. 20110. The ATCC accession number is PTA-6708 deposited on May 11, 2005. The deposit will be maintained in the depository for a period of 30 years, or 5 years after the last request, or for the effective life of the patent, whichever is longer, and will be replaced as necessary during that period. DNA molecules of the present invention can be isolated from the genome of the deposited material and the sequence corrected if necessary, additional DNA molecules for use as probes or primers for the haplotype regions disclosed herein can be isolated from the deposited material.

All publications, patents and patent applications are herein incorporated by reference to the same extent as if each individual publication or patent application was specifically and individually indicated to be incorporated by reference.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,757,011
U.S. Pat. No. 4,769,061
U.S. Pat. No. 4,810,648
U.S. Pat. No. 4,940,835
U.S. Pat. No. 4,959,317
U.S. Pat. No. 4,971,908
U.S. Pat. No. 5,015,580
U.S. Pat. No. 5,094,945
U.S. Pat. No. 5,229,114
U.S. Pat. No. 5,304,730
U.S. Pat. No. 5,384,253
U.S. Pat. No. 5,437,697
U.S. Pat. No. 5,463,175
U.S. Pat. No. 5,482,852
U.S. Pat. No. 5,508,184
U.S. Pat. No. 5,512,466
U.S. Pat. No. 5,516,671
U.S. Pat. No. 5,538,880
U.S. Pat. No. 5,543,576
U.S. Pat. No. 5,545,545
U.S. Pat. No. 5,550,318
U.S. Pat. No. 5,591,616
U.S. Pat. No. 5,608,149
U.S. Pat. No. 5,627,061
U.S. Pat. No. 5,633,435
U.S. Pat. No. 5,637,785
U.S. Pat. No. 5,654,182
U.S. Pat. No. 5,658,772
U.S. Pat. No. 5,659,114
U.S. Pat. No. 5,689,041
U.S. Pat. No. 5,716,837
U.S. Pat. No. 5,750,876
U.S. Pat. No. 5,773,696
U.S. Pat. No. 5,792,924
U.S. Pat. No. 5,801,030
U.S. Pat. No. 5,824,877
U.S. Pat. No. 5,942,664
U.S. Pat. No. 5,958,745
U.S. Pat. No. 5,981,840
U.S. Pat. No. 5,985,605
U.S. Pat. No. 5,998,700
U.S. Pat. No. 6,011,199
U.S. Pat. No. 6,013,864
U.S. Pat. No. 6,031,154
U.S. Pat. No. 6,040,497
U.S. Pat. No. 6,063,597
U.S. Pat. No. 6,063,756
U.S. Pat. No. 6,072,103
U.S. Pat. No. 6,080,560
U.S. Pat. No. 6,093,695
U.S. Pat. No. 6,110,464
U.S. Pat. No. 6,121,436
U.S. Pat. No. 6,140,085
U.S. Pat. No. 6,160,208
U.S. Pat. No. 6,166,292
U.S. Pat. No. 6,171,640
U.S. Pat. No. 6,184,440
U.S. Pat. No. 6,228,992
U.S. Pat. No. 6,316,407
U.S. Pat. No. 6,380,466
U.S. Pat. No. 6,384,301
U.S. Pat. No. 6,399,861
U.S. Pat. No. 6,403,865
U.S. Pat. No. 6,444,876
U.S. Pat. No. 6,476,295
U.S. Pat. No. 6,476,295
U.S. Pat. No. 6,476,295
U.S. Pat. No. 6,486,383

U.S. Pat. No. 6,506,962
U.S. Pat. No. 6,531,648
U.S. Pat. No. 6,537,750
U.S. Pat. No. 6,660,911
U.S. Pat. No. 6,768,044
U.S. Pat. No. 6,774,284
U.S. Pat. No. 7,030,215
U.S. Publn. 20020132350
U.S. Publn. 20030083480
U.S. Publn. 20040177399
U.S. Publn. 20050064474
U.S. Publn. 20050208489
U.S. Publn. 20050246798
U.S. Publn. 20060021093
U.S. Publn. 20060021094
U.S. Publn. 20030028917
Abremski et al., *Cell,* 32:1301-1311, 1983.
Allard, "Principles of Plant Breeding," John Wiley & Sons, NY, U. of CA, Davis, Calif., 50-98, 1960
Beachy et al., *Ann. Rev. Phytopathol.,* 28:451, 1990.
Berno, *Genome Research,* 6:80-91, 1996.
Charest et al., *Plant Cell Rep.,* 8:643, 1990.
Cheung et al., *Theor. Appl. Genet.,* 94:569-582, 1997.
Comai et al., *Nature,* 317:741-744, 1985.
DeBlock, et al., *EMBO J.,* 6:2513-2519, 1987.
Dellaporta et al., *Stadler Symposium,* 11:263-282, 1988.
Dempster et al. *J. R. Stat. Soc.,* 39B:1-38, 1977.
Eichholtz et al., *Somatic Cell Mol. Genet.,* 13:67, 1987.
Elliot et al., *Plant Molec. Biol.,* 21:515, 1993.
European Appln. 0 242 246
European Appln. 0640141
European Appln. 0797673
European Appln. 1308516
European Patent Appln. 0154204
Ewing et al., *Genome Research,* 8:175-185, 1998.
Excoffier and Slatkin, *Biol. Evol.,* 12(5):921-927, 1995.
Fehr, In: *Principles of variety development*, Theory and Technique, (Vol 1) and In: *Crop Species Soybean* (Vol 2), Iowa State Univ., Macmillian Pub. Co., NY, 360-376, 1987b.
Fehr, In: *Soybeans: Improvement, Production and Uses,* 2$^{nd}$ Ed., *Manograph.,* 16:249, 1987a.
Ferreira et al., *J. Hered.,* 91:392-396, 2000.
Fisher et al., *Plant Physiol.,* 102:1045, 1993.
Fromm et al., *Proc. Natl. Acad. Sci. USA,* 82(17):5824-5828, 1985.
Geiser et al., *Gene,* 48:109, 1986.
Giddings et al., *Nucleic Acid Res.,* 21:4530-4540, 1993.
Glick et al., In: *Methods in Plant Molecular Biology and Biotechnology*, CRC Press, Boca Raton, Fla., 1993.
Gordon-Kamm et al., *Plant Cell,* 2:603-618, 1990.
Hardy et al., *J. Virology,* 71:1842, 1997.
Hinchee et al., *Bio/Technology,* 6:915-922, 1988.
Ikatu et al., *Bio/Technol.,* 8:241-242, 1990.
Jefferson et al., *EMBO J.,* 6:3901-3907, 1987.
Jefferson, *Plant Mol. Biol, Rep.,* 5:387-405, 1987.
Jones et al., *Science,* 266:789, 1994.
Katz et al., *J. Gen. Microbiol.,* 129:2703-2714, 1983.
Knutzon et al., *Proc. Natl. Acad. Sci. USA,* 89:2624, 1992.
Lacape et al., *Genome,* 46:612-626, 2003.
Lawrence and Solovyev; *Nucleic Acid Res.,* 22:1272 1280, 1994.
Lee et al., *EMBO J.,* 7:1241, 1988.
Lee et al., *Plant Mol. Biol.,* 48: 53-461, 2002.
Lewin, In: *Genes V*, Oxford University Press, NY, 1994.
Lincoln and Lander, Mapping Genes Controlling Quantitative Traits Using MAPMAKER/QTL, Whitehead Institute for Biomedical Research, Massachusetts, 1990.
Luo et al., *Plant J.,* 23:423-430, 2000.
Lyznik et al, *Nucleic Acids Res.,* 24:3784-3789, 1996.
Marshall et al., *Theor. Appl. Genet.,* 83:435, 1992.
Martin et al., *Science,* 262:1432, 1993.
McCallum et al. (2000) *Plant Physiol.* 123:439-442, 2000.
Miki et al., In: *Methods in Plant Molecular Biology and Biotechnology*, Glick and Thompson (Eds.), CRC Press, Inc., Boca Raton, 67-88, 1993.
Miki et al., *Theor. Appl. Genet.,* 80:449, 1990.
Mindrinos et al., *Cell,* 78:1089, 1994.
Misawa et al, *Plant J.,* 4:833-840, 1993.
Misawa et al, *Plant J.,* 6:481-489, 1994.
Ow et al., *Science,* 234:856-859, 1986.
Padgette et al., *Crop Sci.,* 35:1451-1461, 1995.
PCT Appln. WO93/19181
PCT Appln. WO96/30517
Pen et al., *Bio/Technology,* 10:292, 1992.
Poehlman and Sleper, In: *Breeding Field Crops*, Iowa State University Press, Ames, 1995.
Potrykus et al., *Ann. Rev. Plant Physiol. Plant Mol. Biol.,* 42: 205, 1991.
Przibila et al., *Plant Cell,* 3:169, 1991.
Rieger et al., In: *Glossary of Genetics: Classical and Molecular,* 5$^{th}$ Ed., Springer-Verlag, NY, 1991.
Rodriguez et al., In: *Vectors: A Survey of Molecular Cloning Vectors and Their Uses*, Butterworths, Boston, 1988.
Rogers et al., *Methods In Enzymology,* 153:253-277, 1987.
Sambrook et al.
Sathasiivan et al., *Nucl. Acids Res.,* 18:2188-2193, 1990.
Shah et al., *Science,* 233:478, 1986.
Shiroza et al., *J. Bacteol.,* 170:810, 1988.
Simmonds, In: *Principles of crop improvement*, Longman, Inc., NY, 369-399, 1979.
Sneep and Hendriksen, In: *Plant breeding perspectives*, Wageningen (Ed.), Center for Agricultural Publishing and Documentation, 1979.
Søgaard et al., *J. Biol. Chem.,* 268:22480, 1993.
Song, Q. J., et al, *Theor. Appl. Genetics* 109:122-128, 2004.
Sprague and Dudley, In: *Corn and Corn Improvement,* 3$^{rd}$ Ed., Crop Science of America, Inc.; Soil Science of America, Inc., Wisconsin. 881-883; 901-918, 1988.
Stalker et al., *J. Biol. Chem.,* 263:6310-6314, 1988.
Stalker et al., *Science,* 242:419-423, 1988.
Steinmetz et al., *Mol. Gen. Genet.,* 20:220, 1985.
Sternberg et al., *Cold Spring Harbor Symp. Quant. Biol.* 45:297-309, 1981.
Sutcliffe et al., *Proc. Natl. Acad. Sci. USA,* 75:3737-3741, 1978.
Thillet et al., *J. Biol. Chem.,* 263:12500-12508, 1988.
Wright et al., *Plant Journal,* 44:693-705, 2005.
Zukowsky et al., *Proc. Natl. Acad. Sci. USA,* 80:1101-1105, 1983.

What is claimed is:

1. A method of breeding a transgenic corn plant comprising the steps of:

providing at least two transgenic corn plants, each corn plant having at least one transgene inserted into its genome;

determining a map location of the at least one transgene in the genome of the at least two transgenic corn plants using at least one DNA marker in the genomic region flanking the transgene insert; and selecting at least one of the transgenic corn plants for breeding, wherein the at least one transgenic corn plant that is selected has in its genome the at least one transgene that is genetically linked to haplotype C1W19H14; and crossing the selected at least one transgenic corn plants with a second corn plant to produce one or more progeny plants comprising the at least one transgene linked to haplotype C1W19H14; and wherein the at least one transgene and the haplotype are linked at a genetic distance of 0 to within about 5 cM.

2. The method of claim 1, wherein the method further comprises selecting a progeny plant of the at least one transgenic corn plant selected for breeding by marker-assisted selection.

3. The method of claim 1, wherein the method further comprises selecting a progeny plant of the at least one transgenic corn plant selected for breeding by detection of expression of the at least one transgene or expression of a transgenic agronomic trait.

4. The method of claim 3, further comprising the step of crossing the progeny plant with another corn plant to produce additional progeny plants.

5. The method of claim 1, wherein the genetic marker is a DNA marker selected from the group consisting of SEQ ID NO: 33-40.

6. The method of claim 1, wherein the at least one transgene encodes a protein providing an agronomic enhancement selected from the group consisting of herbicide tolerance, disease resistance, insect or pest resistance, altered fatty acid, protein or carbohydrate metabolism, increased grain yield, increased oil, altered plant maturity, enhanced stress tolerance, and altered morphological characteristics.

7. The method of claim 6, wherein the herbicide tolerance is selected from the group consisting of glyphosate, glufosinate, sulfonylureas, imidazolinones, bromoxynil, dalapon, dicamba, 2,4-D, cyclohezanedione, protoporphyrinogen oxidase inhibitors, and isoxaflutole tolerance.

* * * * *

SEQUENCE LISTING

<160> NUMBER OF SEQ ID NOS: 63

<210> SEQ ID NO 1
<211> LENGTH: 664
<212> TYPE: DNA
<213> ORGANISM: Glycine max

<400> SEQUENCE: 1

```
attcagaagg ctgttaaaac cccctcaggt caccaccact aaacaagaca acaagacaat      60
aacagataaa agcctagttt gtcttgcatg cacttacatg cacctttcat ttttttttct     120
tgcatgcatc atggtcccct actaatacca tttatcttca actattcccc cctctcccaa     180
aatcattcct tgcccttcaa cttttcataa ttgtcttaat taaatgtttg gattaaagtc     240
tataaaagta tcacaaggct tactttttca aaactggata tctaggtaaa attttactct     300
caaacatagt tttgggagta accaaacatt accctaaact gattttaatt tcaaacatat     360
acttttaaac cctcccactg gaaatccgaa cacatcctaa gatgacttat tatatttgca     420
tctatctaat aataataata aaagtaaatg atttttatat tgatacttaa ttatgagttg     480
ttttatgata tgtttattga cttttatagt gattagtatc tactttaaaa atcatatcta     540
ttttggacta gctgagagtg tttatattga caatacatag aaattaaatt ttaagaataa     600
gaaaatgata atcatatttt aggatattgg ttaagaataa aataaaaagt tttattgaaa     660
aaat                                                                  664
```

<210> SEQ ID NO 2
<211> LENGTH: 1156
<212> TYPE: DNA
<213> ORGANISM: Glycine max

<400> SEQUENCE: 2

```
aaagccaatc agatgctact gagtaaaatc agaaaaaatg tgaactaaga gcaatgacaa      60
gagtcaagaa tgctatacct gctgctcagt catttgaaga aaagcaatag tatagtacac     120
caattctctg atattagcca caaccaccta tagaaatgca aaccatagat caaagtaatg     180
atacaattga acacaatcag cagaaaaata agatttcaag aatgttctga accaaacctt     240
tcccagtctt ggattaccca caatggtcaa catgagttca aacagctgta aataacaact     300
tagataaaaa tgataattca aaaattatta caagaaatga aggaaacaca aacaaaaaac     360
catgcaaacc tgatttacgc aagttttaga cagatctcag ccagtttatt atttaaaatc     420
ctataattat aattttttat catttccata caataatcca gcaaaactat acgacactaa     480
taaaaggtat agatcaaaca aagaggttcc tttcaatagt aagctgatga agccatcatt     540
gcagtgacta cagtatcccc tgtgaattcc agtttgacta atttgaaatt taggactgtc     600
ttccttgcca aataacaagt taaaggatat cattctagca gctgattcag tttgacactt     660
catagtgacc tttctctctc tggaatactg acaactatgt acagtttaaa ttaaacaatc     720
aagttaacag cagttttctt tggggcagta tgcagatgat acggtttcct ttgggacagc     780
aacattggca aatgtaagag caatcaaggt gatgttgagg agctttgagt tggtatcggg     840
attaaagata aactttgcca acatctgttt ttgggcaatt gggatgactg agcaatggat     900
gaacagtgct gtcagataag ttgcagaatg atgtcagtac tcttttctta tttgggtatc     960
tctattgggg caaactcaag acgtagtgag atttgggatc taatagtcaa gaaatgtgag    1020
agaaaattgt caaaatgaaa acaaaaatat ctttctttcg gggaagggtg actttgatta    1080
agtcagtcct aaactcgatc cctaaaattt ttttcttttt tcaaggctcc aaagaatgtg    1140
gtggataggt aggtga                                                    1156
```

<210> SEQ ID NO 3
<211> LENGTH: 657
<212> TYPE: DNA

<213> ORGANISM: Glycine max

<400> SEQUENCE: 3

```
atagttcact aggtttgtac tcatgccata atatgccaat ctttcacagc attcatttcc     60
tgacataatg tttttagcac cttagtgcga ttttaatact gaaatatgca taaaagatgg    120
tatcgaaatg aaagaagaaa aaaaatccaa taccaagtat gaagcggcat gctttccaat    180
ttccagtttt tttcttgatg gcaggctttt tgtaaatatc aactgtccca tcttctgtgt    240
ataaactatc ttctcccaca tcatgtgatt ttttgacatc tcccatggtt tcacagcaga    300
tttcctattt gctgcttctt gttctctttg atatctacta caaatgtctg tttgcagggt    360
gctggaaatg agtaaacaaa ataatcggca aaaggtacac gaaaattaaa cagattgcta    420
tcatgaattt catattataa atacttgatt tgagggtgtt tatgaagtag gaatagcaaa    480
gagaggttca gcaaagcaat gaatatgtta gctcatgaag ctccaatcac aatccttcgc    540
aaacacattt gatggcaaca ttgtgatttg ggattattag tggtacaaag tgatagttat    600
aatcacaaag aattaatgta gaactgcagg tgacttagga ggtccgggtt cgacccg       657
```

<210> SEQ ID NO 4
<211> LENGTH: 659
<212> TYPE: DNA
<213> ORGANISM: Glycine max

<400> SEQUENCE: 4

```
atttgggcgg cctacacttt tttgaaaatt aaaatatact tttgtgtagc taatttccgt     60
tttgcatgtg tgtgtgtgtg taatggagag agagatagag agaaagagtt agtttggttc    120
ctagtggcac tgaaattact accaaatctc caaaagtagc tatggagtta tttaggatgt    180
ctaatgagtt gagtttatgg tcttatttat atgtggaaat aatgatttat taatccagag    240
cagatgagtt aaaagtttct ctagagaatg gtagtttcta aatgaataaa taggatagaa    300
tctctagcac tcaaagaatg aaagaatgtt tgcattttat tatcacctga gccaatttca    360
gatatctcga ttatttcctc ttaatatccc atggcaacat tcattgcgtt aagccaacat    420
tttaaatgaa agtatctgtg atctccaagt ctttgatatt catttgtcta ttccaaattt    480
tggttccaac tggcttcgaa agctttgatc ctcctccctg ctttcagcat gatttcctca    540
ctcttcttga actttccata ctgaggaagt ctgagacaca atggtaaaac tatcatggtt    600
atggaatcca tgaaacaaac atcattattt tctattaagc tctgaattgt agaaataca     659
```

<210> SEQ ID NO 5
<211> LENGTH: 372
<212> TYPE: DNA
<213> ORGANISM: Glycine max

<400> SEQUENCE: 5

```
cattcatcag aagtgctcaa agcatttaat ttcagtgcca aagcactgca acttttcagc     60
tcagacaaaa caaacttgct agcttccttg gtaactgtgg aggatttgat agacttgaaa    120
accttctcaa cagattcttg agcacatctg cgtacctaaa aagcaaacaa accacaacac    180
aatttaaaca aacaaaaaat ccataagctc agagtaatga aatgattaat aggcatggac    240
caatgtctcg aaatcaaagg tcatatcata accaaatgct gattgcattg taaggtaaaa    300
ccatcaccaa atctatacat aattggatat aaacaaggtt taaaactaaa gttgcagaca    360
cattagcagc ac                                                        372
```

<210> SEQ ID NO 6
<211> LENGTH: 1448
<212> TYPE: DNA
<213> ORGANISM: Glycine max

<400> SEQUENCE: 6
aacagaactc tatggccgca agacaagata gaccaaagag gaaggacccg gcatattaaa 60
agcagtgaca aagtaggaaa attgcactca tttacgatca acccaggttc ttgtagatct 120
agagtactag taaggttctc taatcactta tggctcttaa tgttgaatag ccagaagtga 180
taaaatcaaa tcaaataacc ccctagggtc ggcctagtga cggggttttt ggtagcatgc 240
acaaagtctt agattgtaat cttgttgagt cattgtacac caaataaata aataaataaa 300
attaaaatta atgtaaaata tgataaatgc aagtggaatt tatttccaac taatttatgc 360
tcgttctcaa cataaaaaat caagagattt gttgtgcata actctttctt aagccatata 420
tcatgactct tacctgctta gctgtcgcaa aattcagtag cgcttcacat tcatcaagca 480
tggctttttc cctagctgat acaacagcaa cttcagacat taaactattc atgccctcca 540
cctattccag acacacacac aaaaaaaaaa aatggtgtca gccttaaggc tttagggatt 600
taccattgaa tcaaaaagga aaatcattag gaagaaaaaa catacagtta gtagaagaaa 660
aaaagtttga tactaaatgt gtaggcctag aaaatagcaa atgctagtgt gatattgtga 720
gtcaaaccag tagaactcct aaaaaagtaa cacaccccgt gacagcaaag ggcagatagc 780
agatcccatt gcttgcatgg catcaacagc tgaatagata gcatgcttca aatgttcaat 840
atctgcctga aaaagtgtaa acacagtaat gatgttagtg tctctttgca cgcatcgaac 900
caaaagaaca gaaaccacca tacatacctt tgcccctcca gttagaggaa gacgaagagt 960
acttgcctcc aagtcttcta cagccccgga taaggcatca atatgatcac tttcaagtac 1020
agcccagtca tcaaggtagg ccatctgtgt cattaattgt aaaaggacta caatttaaaa 1080
aagtatcaaa aaaaagttga atcatttaaa taagaaaatg gtttcatata tgacttgtaa 1140
tcatatccac cattaataat atgagttatg aataccatgt tatgacagac tagcataaac 1200
aattaaacat aacttttcaa tgtgcagggc caacatcttg ctgagtatat tttcctcatt 1260
tataaacttc acaataaata tctctagtta aattaccaaa aatgaaaatc gggaaaaaaa 1320
aaaaagaaag aaagaaaaag taattgtaat gtatcatcaa caataaatatc gcacatagaa 1380 tgataaatat ttcaggcaag agagaagtat tacttgatca ttcaaaatag aattcagctt 1440
cagctcaa 1448

<210> SEQ ID NO 7
<211> LENGTH: 922
<212> TYPE: DNA
<213> ORGANISM: Glycine max

<400> SEQUENCE: 7
agtttgctag gaagtgggtg ccattctgca agaaattttc tatagaacct agagcaccag 60
agatgtactt cagtgagaaa attgattacc tcaaggacaa ggtgcagccc acctttgtta 120
aggatcgtcg agctatgaag gtctgtatca tatctatcag actagtactt gaacacatgg 180
gagtttaaaa gttagtttaa agcttattca gtgttaattg ggtgtttgac agagagaata 240
tgaagagttt aaggttagga tcaatgcact tgtggcaaaa gctcagaagg ttcctcaagg 300
aggatggatt atgcaggatg ggacaccatg gcctggaaat aatactaagg atcatcctgg 360
tatgattcaa gtctttcttg gtcacagtgg aggtcatgat actgaaggaa acgagcttcc 420

```
tcgtcttgtt tatgtttccc gagagaaaag gcctggattc caacaccaca agaaagctgg    480

tgctatgaat gctttggtag atttttttga gcagtttttg ttgttcctat gatgtccatt    540

cacctttata tgagacacaa ttccttgaca cttccaatta ttgctgtgat ttgcagattc    600

gggtttccgc tgtgctcaca aatgctcctt tcatgctgaa cttggattgt gatcattatg    660

tcaataacag caaggctgct cgagaggcca tgtgcttttt aatggacccc caaactggga    720

agaaggtctg ctatgtccaa tttcctcaaa gatttgatgg cattgatagg catgatcgtt    780

atgctaatag aaacacggtt ttctttgatg taagtcactg caagaaacac agcatcagca    840

tagcatggcc ttttctttga agcatttgac tatttttttt tggtagtgta agctaatact    900

aactatttct tcttctttgt ct                                             922


<210> SEQ ID NO 8
<211> LENGTH: 730
<212> TYPE: DNA
<213> ORGANISM: Glycine max

<400> SEQUENCE: 8

tccctattat tcactgaagt aatgaataag tcgttgaaga aagttgggca tgtcattatg     60

tcaaaatgct tctgacttct gagggtcaaa agtttacacc tcttttctat tttcgtaaaa    120

ttcctgagga acatttttct tctgacatgt aaagtgaaat tttatagctc attgctgtac    180

tgccgtttaa tatctgacaa tcattgaagt taattaaact atctcataaa agttgttggt    240

gatgaatgtc tggaggtgta agcgcaaaat ttgcgaccag ttaatgaatg tcttatcaac    300

gaaaatacgt gtactactaa tcaaccaaca tatgtggctt aaacaatcct agtttgccag    360

tagtataaat gctggggtta cattatcagt agatgttttt attagagaac caggtcatga    420

tcttcagttg aatattgcca caagtatgac atgtgttatg cttgtttttt ccatcagaat    480

agagtagtgg aaaaaaatgc taatctgtga caaatttagg ttgtgtaagt tgaagtagtt    540

gcatggaatg cgcttcatca tgatccttgt gtcagtttct aattttcaat gttattttgg    600

cgtaaacagg ttgaggaata tagccttcgg acgcatctca tgcagatcaa gcaaataagt    660

aaccaatctc ggaaattcaa acacgcatga ccctgacctg cttctacgct aacaagaagt    720

cttttgcagc                                                           730


<210> SEQ ID NO 9
<211> LENGTH: 717
<212> TYPE: DNA
<213> ORGANISM: Glycine max

<400> SEQUENCE: 9

tcttatttga tttctccaat gatatgcata tagtggtgtt taaccatgtt tcttgacatt     60

tatttgtgtt ctatttgatt atgtgactgc tccagaatag agtatttatg caatatcttg    120

gtaatggaaa ctaacaaagt ggaattaatt aactcattgg agccattcat tatgattgtt    180

tctttcaaat tgtctattga gttcaatcat ttgttgcttc tattgatttt atttaatatt    240

ttagtaggca tgatcggtcc aggggctgta gaaatatagt gaaggatttg aaagtctttg    300

acacattcaa tacttggttg cattatgaat atgttgaaga caaattatag aagataaatc    360

taaggagcaa ttttatatat caacaagcag caagggaata tgttcgaaca gatggtgggc    420

acataggttt ggagctgtca tgagcttaat tcatttgagg atgacccata ttttaaccgt    480

caaaagcaaa acatagaata aaaggaatat tgattctgtt tgcattttgt ttggggtact    540

ggctagacta gatacgtttt cctggtccaa tggaaacctt tggatcgttg gttgatttga    600
```

agttagtaat atgctgaagg aggaagctac aagagaagtt tgcatttcac gatcattttt 660
ccttatgtat aggttgtttt ctattgttta ctcacatttt cagctgcagg catgcaa 717

<210> SEQ ID NO 10
<211> LENGTH: 807
<212> TYPE: DNA
<213> ORGANISM: Glycine max

<400> SEQUENCE: 10
tgcataatca accaactgat atgacatttt ctgtggaatg gacagaaccg ttattatcat 60
gatgttaatc agtagatcat ttgccatctg gcttccagat gttaatctct tagtagaatt 120
tttcattgcc tagtattgag aataaaacag atttgagact taaggttctg tatgcaatac 180
aatgaattgt ttattagcat tgtctacttc ttgatactga tggttgtcat tacagtaata 240
tgtcgaaatc tataataact aataatcact taagcaacaa gttaaattct gtttttggta 300
ttttgtcatg ggtgtcttta atgcaagttt atatctttga tgcttttttg gttttatttt 360
tacaaaatag tagatgaagt tcattaagat gtttttcctt attgattgtg aaatggaatg 420
catgataata tttggtgttc tgtctacctc tcctgaatta gaccagtcag tttaattctg 480
ttgctctctc tgttttattt tactctcaat ctttgtgagt tttcggttc acttgagttg 540 tactgtctct agaaggtcct attactttat tggtcaagaa aaatatagaa ggatattaat 600
ccaaccttgt gatttgtgtg cattacactc atacacattt tatgttcata tagtcatctc 660
aatctaatta gttgttctat gcaaactttg ttgtggaatt gaactgcttc ctgctgtgca 720
tttaacttgc cttgcttact gttctccttc tgtgtgtctc aggttagaaa ttctttgaat 780
gctcagcctt ggatccataa taatctg 807

<210> SEQ ID NO 11
<211> LENGTH: 839
<212> TYPE: DNA
<213> ORGANISM: Glycine max

<400> SEQUENCE: 11
caaacttgca tgcctgcaga ctatatggca ccgcccctat agtgcccctt ccaacgatta 60
cctagaattt aatttgatct tctgaaggta gatgaataaa taaataaacg tgtgaaaata 120
aaacagtaag tacatgccag tacgtaataa tgtgaactag tttgtataca tgaatttagg 180
tccaatgctg caaaagacct agttagactt ggaacataaa aggatatatt taaatgactc 240
tcaagattaa ctaaataata cacagacaaa tcagataatt aaactgcacg gccactaagg 300
gatcagcata tgtgaaagtc tcagagagca gacatgtcgc tagttatata taaatcaagc 360
tgattttatt atctatatgg gaatcaaata caagcttaat tctcttttgc tagcttcaat 420
ttggatacac ataattccaa cctccaccaa ttgataacaa atactagtaa tgtacacatg 480
ctattgtgcc cccgggtagc ttaactcttg aaaaacacat tctcgtggca tctcttgacg 540
cacaccctcg taattcgaag caacaagagg aggataaatc agagaactgg tttcacccca 600
atcagtactt tgtccacaac ttgaagaagc acaagcacca cccattatct tatcggtaat 660
catttcctcc ccatagaaga actccaacga cccacctaat aacctttgag aataatcatt 720
agcagaaacc atttccccaa ctgtagtggt agtgaaactg ctttgtcctt gcaccaactc 780
agcacggtac tcattgctct gaccaaactg tacttggttg ttgccaatag agttcatgc 839

<210> SEQ ID NO 12

<211> LENGTH: 751
<212> TYPE: DNA
<213> ORGANISM: Glycine max

<400> SEQUENCE: 12

```
aaacactggc ttcggattta tcacttgtaa gtagagtttg ctaactaaaa tgctttgtca     60
ctctttattt tcaggttttg ttctgatatc caaaatcctg gctatgttga ttgccattca    120
aattgtaata agtctacatc tcaagcgtct ttgtttttgt gttccgactc caacagtaga    180
agaaatggtg tttttggtag accactttgt gtgaacccct ctggcaggag aaacctagtt    240
ggtccagctt tttattctct ggagactagt gcttatgacg tggctgcttt agaatctcct    300
tcccgtgttg cagaagaaaa agttggtgtg ctgcttctca atctaggagg accagagaca    360
ttgagtgacg tgcaaccttt tctgtttaat ctttttgcag atcctgtatg ttagtttgta    420
tttgtgcttt ttctactgtt gatttttctt tttcctgttt atgtaaattc cattagcatt    480
agtacatgtt catatgattt gtatgctaat gtgtttcttg tattgacata ggatatcatt    540
cgtcttccaa ggttgtttcg gtttctccag cgaccattgg caaaattgat ttctgtactt    600
cgggctccta aatccaagga agggtatgct gctattggtg gtggctctcc tttacgaaaa    660
attacagatg accaggtgga gtttaaattt tttggttttc ccattatctg ctttgtggag    720
cttttatctt tctgcaacat gaatcttttt t                                   751
```

<210> SEQ ID NO 13
<211> LENGTH: 663
<212> TYPE: DNA
<213> ORGANISM: Glycine max

<400> SEQUENCE: 13

```
aatatgaaga agtacctgct ttaccattca acttagtgac tgtaagtatt caatactaga     60
gccaagttca cttttctatt tagctacata ctaggggggg ttctcttggt aaaaagaaac    120
tatctatact tatatgttat ggaattacat gactttcatg atacaaatca catgaatatc    180
aatagttgca agtagttctt taatgattta tatttcttag gaacatgact tgtgcataac    240
ttctttgagg tcaatccacg gcttagagta attctgggaa cccgtttgca tcattgtaaa    300
caggcatttc acactttcga atgcatcaaa tgaagcaaca ttttttttata attggcattc    360
aatgtccatt tggatggttt gaactgataa ccatttggat ggtttttaca attggcatct    420
gtgtcttcag gaaggggact tgagcaggac agcttccttt gcagatgatg gagaggtttt    480
agatggaata attactcgaa gccggggtga ggttagacgt gtttgcagtc caaaggtgat    540
gaaatccact ccaaacctat cccaagagtt aacaagtcca aggctcacag ataaagtata    600
cagccctcgg ataagccatc tcagaggaaa tcaaagccct cgaggtgttg ggagaggatc    660
att                                                                  663
```

<210> SEQ ID NO 14
<211> LENGTH: 713
<212> TYPE: DNA
<213> ORGANISM: Glycine max

<400> SEQUENCE: 14

```
cttaagtctg aaaacaattt gtctacttgt acataatctt tatcatggac aaagtatcaa     60
gaacagaaaa tattttatat attgtctact cttgcctcat tcttacacat ctttatttta    120
tttattttgt ttcaagttat ttgttattga aaaagataaa agtgttaact gtttttttaa    180
taatattcta atttaaataa attcaaacct atatttgagc tcttttttta atgaggataa    240
```

```
tttaatattt tttatgttat aacttgtgta attaatattt ttttgagaga actcagcaaa    300

aaataaataa atttttgaga gaaaaataat atttttttta aagaagtgtg tattatttta    360

aaaaataaat aatatgagat ggaggcaaca tgtgatttta acaatgactt gtaacatcta    420

taagctcaaa atttttgaaa aatgaactgg cgtaggataa aattaaacta cctggataaa    480

gcaaaggttc ttcccaattg gttatttaaa gcaatcttct ttgtataatg gataccataa    540

cttcaatctc ttaactacca tgatttgatt gaagcgatcg atctcacaaa gatgttcctt    600

tcaatattct taaactcaag tacaattttc cctcaaggac ccactatgtc tatattccat    660

tggattacat agtaaaagca aaccaataat ttctctacct ttagctgcat ttt           713
```

<210> SEQ ID NO 15
<211> LENGTH: 534
<212> TYPE: DNA
<213> ORGANISM: Glycine max

<400> SEQUENCE: 15

```
cttgcatgcc tgcaggagac tttgagaaag cacacttcag ttgtttaccc gatataggag     60

agatacaagt taaagggtta atggtaagta ctttactttc tgtttagtat ctatgcatcc    120

ttttatgaat ttctgcacca atgagttttt gctcaagtta ctgcacattc tcctaggtga    180

agcgaaaatc atgcttctac tacctgcctg attcgttccc tatacagtat gctttccctg    240

caatcagagg aacatggttt cttcatgtgg aagtgaagca tttaaagcgt ttgcgcattc    300

cgtgtccacc tggtgatgca gctgttcttt caaaacataa ggacttaaag acctgcaatg    360

gtgaggataa ggcaaaatgc aacagtgagg aaaataaaat ggaagggttc caaccccgtt    420

catgttttgc agaagagcat gaaactacta atcatgtttc aaagaagctg aacaaaaaga    480

gaatttctaa tgaaaaccac acgcagaatg aagccactgg aatgccagaa agat          534
```

<210> SEQ ID NO 16
<211> LENGTH: 433
<212> TYPE: DNA
<213> ORGANISM: Glycine max

<400> SEQUENCE: 16

```
ttgccaatgc agctgctggc ttgagtgcag ccatggcagc tcagcttgtg tggacccctg     60

ttgatgtcgt gagccagagg ctgatggttc aaggtgtttg tgattcggga aatcctaagg    120

cttcagctct tcggtacatc aacgggattg atgccttcag gaagatcttg agcagtgatg    180

gtcttagggg cttgtatagg ggttttggga tatcaatttt gacctatgcc ccttcaaatg    240

cagtttggtg ggcttcatat tctgttgcac aaaggatggt ttggggtgga gttgggtact    300

acttgtgcaa gggaaatgat agtgcactga agcctgatac aaagactgtg atggcagttc    360

agggagtcag tgcagcagtg gctggtggca tgtctgcttt gatcaccatg ccactggata    420

ccatcaagac aag                                                       433
```

<210> SEQ ID NO 17
<211> LENGTH: 554
<212> TYPE: DNA
<213> ORGANISM: Glycine max

<400> SEQUENCE: 17

```
aaaaaaaagg acaatcatta aacacgtatc taaaatgcat ttcatcaaaa tgaaaaatta     60

tgcaatactg aaaatccatg cgtgttataa aggcaaacaa aatgaacttg gagagcaatg    120
```

```
caacaaagta ctttttacag tcaatgtgca ctttaaaaaa tagtatattt catacttaca    180

taaaagagct gaatgagtgc aagacgtacg aaagaataaa atttcaaagt gccacctaag    240

tcacagagtt tatgagaaac aaactgtgag ctttggtcag gtaatatcca ccacaatgca    300

gggatgacaa ccgagtttag gacgaatata ctgcacaaaa atttaaaaga tgttgaaatc    360

attaaacacg tagattttag attcatgatt tgttcaggac aatcaatcca tggatgacaa    420

aaatatgtac aatcagattc cttcgagtca ttatgtcaaa agtatacata atccaatttc    480

tttgccacaa aatttcattc actgtgttga aataaattga agctagtttc acttctcctt    540

ctgcaggtcg actt                                                      554
```

<210> SEQ ID NO 18
<211> LENGTH: 810
<212> TYPE: DNA
<213> ORGANISM: Glycine max

<400> SEQUENCE: 18

```
tgagtttaat catgtatctt ctttttcaat gcttttggtt ggacattaaa gccatatttg     60

tttggatttt gtgccatata ctatcaatcc aattttatta agaactaaga cctactagtt    120

tttcaaacaa ggtcagcaat actcaaaaat aaattgccaa gttggaccct gtagttttgt    180

aaatgtatcc caacaattat aattaaaaag tagttgtact gtataatatc tagcaaattc    240

aaaattctaa agtcaatttt ttactgtcta atccaaatgg acgctaagat actagactat    300

tgatactcac agaacattat ctgtagttaa catgaaaaat gtagtttgtg gttttgatgc    360

ttcctttttt attttattta agtgacttag tttgtagatt ttactttgca gggagactat    420

catgttgaca gtgaatttg tggtacggac agtgtacagc tgaaaggatc tgagattact    480

gctgaactta agtatctctt aaacttgttg acattgtgtt ggcacttttc gaagaagccc    540

tttcccttgt ttttagaaga aactggctac agtgaagaaa acgttctcct tcgagaagcc    600

aaagcaggag taagtcttgt ttgaatttta ggaaaaaatg ataataattc aatatctgta    660

ctgtgttgac taagtcattg atagttatta acacacattc tcttttgagg aaggatggaa    720

ggctgaaagc acaagagatg ttgttttatt tagactgata aaatatggga taaaaaattg    780

atgatagatg ccttcttttt gcttcacttt                                      810
```

<210> SEQ ID NO 19
<211> LENGTH: 1222
<212> TYPE: DNA
<213> ORGANISM: Glycine max

<400> SEQUENCE: 19

```
aggtgcagct gccctttgt actcacattg aatcggaaat tgcagactca cgatgcaatc     60

gacgaagatg gtgaagaaaa tgggagtgat acgcccactg atacgccatt aggtattggc    120

cgtgtttctc atcggttaat ccaagcccct gcaacatggt tggagacaat ttcaacattg    180

tcagagactc tcaggttcac gtattcggag acacttggga aatggccaat tggggatttg    240

gcgtttggca tcagctttct tctaaagcgg caggtaatga caacgagtag attttggttc    300

tttattgttg ccctgatttg aagcaactga aaatgccgga aagctgtgtc gtttttttat    360

ctatctgtaa ctttggacac atttaagtag taagtagaat atagaatcag tatttagtgt    420

ggaagccagg tgcatatttt tcaggtagaa ctataattga tctgaaatgg tagttgcaac    480

ctgcacttaa tgtgcaactc acataattca cctaaaggat tgcccgtcac tgacattgat    540

gaatgaaaga gagagaaata tagagaaagt aaaatggaca atggtcatgg aagttatgcg    600
```

agttaggtga actttttcat gtgtaaataa aattgttgat gattaaatgg ttggaagacc 660
aatttaatgc tttccatctc aataaaaaaa attatggtcg ttaaagaaat aatcccacat 720
ttggagagca gttataattt atattaactc ttaagtgttc cttacatgtg ataggatctt 780
tttttcatgg gtgttgtttt tgttttgctt tttaagcctt ctcaacatca cagcagtggt 840
ttgggatcat gacttgcaat atttgaactt cttttgttac ttgttaatca tgatcacttt 900
gaagttgaca tattagatta ttcttggatt ttatgattta catgatatga tttctgttta 960
tactttctag gagagtaata tggctaaggt agcttagaaa tcagactatt ctctacaaaa 1020
tgaatcctca caagattgtt cacatgacct gtgctacttt atatatttga ttttgattta 1080
aatcatatat taagcatttt ttaaggtaga tcagtttcat gacatcctgg actacttaat 1140
ttcttcatct cagctcaaca taaatagatg agaagttgct ctgtaatatt ggttttgtgc 1200
cagtttaatt tgttcatatt aa 1222

<210> SEQ ID NO 20
<211> LENGTH: 682
<212> TYPE: DNA
<213> ORGANISM: Glycine max

<400> SEQUENCE: 20
gcaacaaatg gatgtacaca gtccgagccc tgcataattg gagcaaattg catattccaa 60
cccttaatga gaatacagaa atcaaaactt gataaataaa atacttcaaa tttgcccaca 120
ttggttgcta atagctattg cagagtatac acaattattc cagtaataca aacttgcata 180
ttaccacaga actcttaatc ataccaacat taaaatagtc tctgtagcca ggctttgagg 240
gcacaagaaa gtgcaacaaa tagttgaaaa aacactgtat gttgtggttc actaatctct 300
tatgaaacag gttatgtaga aaggcttcag ttgtcaccta ctaacatcag ttcaccttac 360
acttgtaatc gtagctacat cttgcttccg gaaacaaagc tatgtatcta atcactaata 420
atgacatcaa agtatgaagt aagatatacc ttttcttcag aggtactctt gacgaaacac 480
aggaatgcct ctgagaactg agagccactg gaaccggttc gcaagtcagc aacgcaaggg 540
cattcaaggg ctttctgagt catttcctcc acagactgaa aaatccaaaa tttccaattg 600
ttttcattcg ttcaacctgc caagttgaaa gcaaaagatc aaagcaattc aattcaaacc 660
tcagtgttct gatttccata tt 682

<210> SEQ ID NO 21
<211> LENGTH: 681
<212> TYPE: DNA
<213> ORGANISM: Glycine max

<400> SEQUENCE: 21
actgaaacat tcgaaattcc ttacataatt tattcttatt aaaaataaca gtaatctttt 60
gacttgaatt ggtacagaag tacaattatt ggttgaggct tttatttcac gcataccaca 120
atgaaacaca tttcaatttt tcttacccct ggttaattta atgtaccgaa tttatacatc 180
aaagagaaga taactttcga agtaaaaatg attatcctaa acaccgtatg ataaagtgta 240
taagattgtt caccattact taggtttttg gaaatgtcaa accttagcac tatggtaagt 300
ttgttgcctt gtaacttgga ggtcatgggt tcaaatcctg caaacagcct ctccttaggt 360
aggaacctca tgcattggac tgccattttt gttgctttgg tgtgagcata gatactgctg 420
aattctttga gatgccactt ctcacttatc ccatttttaa cttgcaatct taacttatgc 480

```
ttgtaactac gttcctgaag gcctagaaat ggtgggataa ggatttatgt gttgtttctt    540

gatggatgtt ttgcagacct tcatgctggg tggatcacat gtcactggac aatgaaacag    600

gattggatcc accaggcata agagttaggc ctgtctctgg acttgtagct gctgattact    660

ttgctgcagg tcgactctag a                                              681


<210> SEQ ID NO 22
<211> LENGTH: 1002
<212> TYPE: DNA
<213> ORGANISM: Glycine max

<400> SEQUENCE: 22

tgagagcttc cattcagaac tactatcaag tactgacagt tagcttcaat acttcattta     60

taataaacag aataatcgct taaatgaaat tggtttagtt tcattcacat taatttcagg    120

cacagtgctt tagatgtaat caattcaggg agctgagaaa gaaattccac aaaccctcag    180

attttaaaag ttgaacatcc tcagcttgct gcatcaatta acagtaaaaa agaaaggaaa    240

tgagaaaaaa tgagatttaa gattttatag caatttcatg tgagatatta gagcagatat    300

gagagttgta actctgaaat ttcaactcac tatccaattt tcttccacag tattatcatt    360

gactccatgt aggttattaa ctgagttcag ctgaatcctg tcagttggat ttgagaatga    420

ataatgatgt tgatatttat gtttttatgt tccaaaaggc cacctttggg caaagggaat    480

acaaacaatt acaatgaaac aagtaattat atacagaaaa ctgagaaaag aaaaaaatca    540

acaaatacct gctttctcca tctgaaaatg agcaactcag ggcagggagt tcagatgata    600

actgcttagc atgatcttta gaaccagagc gacataaatc cacaccagaa cttgactgag    660

ataactctga gtgattctgt gcatgaaagt aaattaaata ttaagctgaa tttaggaaat    720

aacgtaatta ctttatcagg aaggaggaag gagaaagcaa aagcatggat aaaaaggaac    780

ttctgcttat gttgctttgg acacaattta taaattttgt aatatgttta gatgttaaag    840

ctgaactaac ttcaaaaaca gaatgagact caacatttag cacactttca agcaaaaatt    900

gttcatgaaa atatcatcag ttcatcactt ttgaagttaa tcaaatgttg cctgcttact    960

ggtaatattt taccaatact atcagcacaa gtagttttat cc                      1002


<210> SEQ ID NO 23
<211> LENGTH: 785
<212> TYPE: DNA
<213> ORGANISM: Glycine max

<400> SEQUENCE: 23

cgacttcgta gcctgcagca agcaaaggcc caactccgtc cagggacggt ccagtacggt     60

ccaagatgat caagctcacc actatgcaca tttctttcgc ctcccaaacc tgaacttgct    120

gcaacagttt taaaagaata ttaatattaa tattaatatt aaagtttcct acagtaagtt    180

attatttaga ataaacataa aaaaaattta tatgaatatt tatttttaat aaataaatag    240

tattcataaa aatgctaaaa tcaagcaagt aattttccta caattttaaa atttgcaaga    300

aaattacata caaatttaaa atccacaaga aagataaact gtgtatttta aattcctgaa    360

aaattaaata caaatttaaa ttccgaagga aaattactag caaatttaaa ttctaccaga    420

aaattatttg caattcaccg aaaaattact tgcaaataaa ttatctgtga aatttctagc    480

agattctttt agtaaaactt tatttataga cacaccactt tttatgtaaa acattttgcc    540

gcagaaattg ttgtatttgt tctagaaaaa ttagcaagaa attttctatg agtttcaaaa    600

ttttcaaaaa attaattatc tactaaggta ttatttagga acccaagtat tggaaattca    660
```

caggtaatta gtaataagaa aaattctata agatatcgta aaaatataga tcacaataaa 720
gcaagataaa cgtacgggga aaaaaaaatg taaaagggaa tctatcttcg tataaactaa 780
cgtat 785

<210> SEQ ID NO 24
<211> LENGTH: 805
<212> TYPE: DNA
<213> ORGANISM: Glycine max

<400> SEQUENCE: 24
tattaggtca gccattatga caacatcgga tatattcgac aatactaagg aactcatcaa 60
ggacattgct gatgattaca aaccagcctc tcctttagcc ttgggatctg gtcatgtcaa 120
ccccaacaaa gcccttgacc ctggacttgt ttacgatgta ggagttcaag attatgtcaa 180
tcttctctgt gcaatgagct ccactcaaca gaacatctca atcatcacta gatcgtctac 240
taataattgc tccaatcctt ccttggatct caactaccct tctttcattg gtttcttcag 300
tagcaatggt tcttctaatg aatcaagggt agcttgggca tttcagagaa cagtgaccaa 360
tgttggggag aaacaaacaa tctattctgc taacgttaca cccatcaaag ggtttaatgt 420
tagtgttgtt ccaagcaagt tggtgttcaa ggagaagaac gagaagctaa gttataagtt 480
aaggatagaa ggtccaatgg tcgaaggctt tgggtatctg acttggacgg acatgaagca 540
tgcggtgagg agccctattg tggtcaccaa tcaggcaccc tcaaattcaa tttccatata 600
gatcaatttt gtgatggata aatgtttttc atatgtttga agttaaaaat atatattaat 660
agaggaaatg ttcgtacatg aatgattatc atttctgata ataataataa tttttttgg 720 aaaagtttta acaccaattt taattttttt tttcttatca cgcacaccaa ttttaattgt 780
tacgtactga aataatacgt tagtt 805

<210> SEQ ID NO 25
<211> LENGTH: 1222
<212> TYPE: DNA
<213> ORGANISM: Glycine max

<400> SEQUENCE: 25
tagatctgca ctcgtgaatg ataacattgt tgaattaagg attttgatgc ttgatgcttg 60
atgcttgact atgagagaga atactattga aaattgaagt gaatacttag aagaagttca 120
tggccttgga atggaatgat catgtgaacc tcattacctg ccgacttggc actgcatata 180
tggatctaat tcaagtcctt ttcatcctcc taaatgcctg tcccttcttc tttagttctg 240
atcctcaact tatccacatt agctttcttt ttctagtatt tacaaggatt gctaaaatta 300
attttatttg taataataaa aatgtttatt attgttgtct ataattatta ataaatacaa 360
ttactcgttt tagtgtacat atttcttatt tctatatacc ctttaatata ttaattattt 420
tcttcataaa ccttcaagat gtaactgttc taattttttt ctaaaaaaac tgttatcaat 480
actttcttta attgtttccc ttttttaaaa taaagataga agcatgaagt gtctcatttt 540
caattattta aataaacaat actttagtta gacacaagtt cgaactataa gtttcccata 600
attttgctcc attatatcct acaatttttg tgaaatatat atattcttac aagataatat 660
tacgcacaac ttttcatcaa aatgttacaa acaactcgag cattttagga catttttttt 720
caagtaaatc ccaggccgaa taatcatcaa cctatgttac attcaccccc aacataaaaa 780
ctaacggggg aagatatcta ttgttagtct gtacatttgt tagtgcctga tctctctcgc 840

```
ctacacagtc gcttgttctt ttaaaaaaaa ccagttagtc accgtttatt ggtcttctcc    900

ttgcctgcaa acaagtttgc cttgtgtcag aattaagcat tactatagag aagcataatt    960

ttcttaaata agattactca ccaaatatag ttgattttaa aggaaatcga attgatgaac   1020

ccttaaatct cagctcccga ttatgcttgt ttctattttg tttctcaata gcactggaac   1080

tattgctagt ttctccggtc agaaagtttg ccactttact taccttttca tggtacacag   1140

caggtggggc aagcttcaat ggaggcaagt tttctatttg cataaatctc tgattcttct   1200

gcaagctgct caagatctgg aa                                            1222
```

```
<210> SEQ ID NO 26
<211> LENGTH: 1177
<212> TYPE: DNA
<213> ORGANISM: Glycine max

<400> SEQUENCE: 26

agtatttttt aaagtacagt gagaaaatgt aaaataaata aataaataaa taaattatct     60

tagctatcat attattgccg ataaaaaaaa atgtcttggc tatcaaagct cttaaagctt    120

accatttagt acggatcctt ccgtggcatc tttatacgcc catttacatg catctatggt    180

actttcagat gcgtatctaa aaaaaaaatt acccaagtta agtatgtata tatgctttga    240

ataataatca gagacaacta aagaagctgg tttctttcat aaaaaaaaaa gaagctggtt    300

tctgttgttt ttctagttat gggtttttgg gatttaaata aagaactcat ttttaagcat    360

gtgataggat ggatatgcca ctattttcaa catcagagaa ggatattata tttttatatt    420

ctaaaggatt attttaatac tattatatgt attgtattta aattatttat aataaaaatc    480

ttaccaagaa aattgaaaga tataaacgtg aaactcgcaa aagaaacatt atagaaataa    540

ttggatttgg gtaaatgata tattaattat attattaata ataatgggac atacgtagct    600

gggcatggaa ggtcattatc accgcagttc tcccattctt ctatctgatc ggcccatact    660

ttctgtttat ttagataaaa ataaataaaa aattgaagat atacaacctc aaacttcaca    720

acccaaatcc ttatttagat tgatgattaa aacaaaattg catacaatac cgtaatattc    780

tgttgaagtg catcgatgaa ttcgttcatg tcagagtcat aaaaattgtc gacttctgtc    840

tgaaggatgg tactatccca aacctgtatg tatatgaagg taaaattaaa catatcatat    900

tgtcgtatat atagtatgtg aagacaagaa atggcaagtt ttaatgcatt ccttcatcca    960

gtttctaatt taaggactca tatttttatc tcaatacatc agattttaaa atgcacacat   1020

tcgagattta aaccatctga tcttcaccta acggtgtcga tctatgaatc catgaagaaa   1080

aaattgactt acatggtgaa gattttgctt ccttttatac cagcgaacag taattgcatt   1140

gcccccatgt ctgagagaaa gccacaatgt agaggct                           1177
```

```
<210> SEQ ID NO 27
<211> LENGTH: 685
<212> TYPE: DNA
<213> ORGANISM: Glycine max

<400> SEQUENCE: 27

agtttgcatg cctgcagcca agctctcgtg gatttggtgg tgttgttcgg gtaaattttt     60

cataatttta tattaaattc ttatgtttct tgatgtgttt tgcaccaaat tcacctattt    120

tgggcataac agacacccac cattgcctgt tcctgctgtc tgtgaaagtc agctgcttta    180

cagctgatgc cgtgggctgt tgtagctctg tcaaactcat ggcctcttaa aaaaaacata    240

ccccagtgtc ataaggctct tcactatgcg aaagtatggg agagggtcat tgtatgtagc    300
```

```
cttgtccttg ctgatgcaag gaggttgctt ccgaattcaa acccatgacc aactggttag    360

gcacaacttt actgttattc caggactcgc cctctagcca aaatgacctt aacaaaaaat    420

agtctctagc taaatgaatt gtgtcaatgg tgttatttta aaggttaaac aaatgtgtat    480

agtccatcag agacaaaaga gtttacacac taaaactgat agcataaatt gtcacaggct    540

gctattatgg atatacaagt tgttccccat ggttttctta catgcggtgg ggatggaatt    600

gtaaagctgg tacggctgga aaataacttg cttggccatg gaattgagtt atgatacttc    660

tgagatcctt tgggttgatg acaaa                                          685
```

<210> SEQ ID NO 28
<211> LENGTH: 1343
<212> TYPE: DNA
<213> ORGANISM: Glycine max

<400> SEQUENCE: 28

```
cttgcatgcc tgcagaaaat tataaaattc ataaaacgct tctacagaaa attcaaaaag     60

attgatttgc tatatatcct atacacttgg acattttagt cgaaacctct atggatagag    120

actttaagga cacaatatta tgaaaaatat tcagctcaaa tattataaaa tgttaaaaaa    180

caatgcatct caatattttt ttgaaaggtg tacttttaac atgtttatga attgtacttt    240

cttggctaat gagtgttttc cctggttaat gttatggatt gtactttgta ggtgtactga    300

tatatttttt ttcattaaat actaatgttg attattcaat tttagaacag tgtacgcata    360

gtatatgact gttattgata aggtatttgt tatcgataag gtgcagttaa tataagcaga    420

gaaagaaact aaaaggttaa ctacatgatt aagcttaagt gatgaaatgg ataatccctt    480

aaaagtcatc catgatttgt atatttggtg ctttgcaaaa acaatcattt aagttcgtct    540

tcaaaatcta gtaacagatt acttaaccat tcttttagat cactacaaat atagtatttg    600

ttttttttaga aggaaaaaat tgggtctgtg gcatcttaat ttttgtgatc acatttttgg    660

ttctagtgat actaacttct tagttcttac aatgtatgta tattttttct ttttacaaat    720

gtcactcttc tcagctggat tcatggtttg aaaactcttt cctcataatg tcaacaggtg    780

gctccctata atacatttta ctcccaattg gaaaagcata tgaatgaagt tggaattgtg    840

cccacagtta accgatggga tgagcctcta gcattgggca tggttgatcc ccatgattca    900

ttatctcatc cagcaggtgt ctctgatgtt caagctgagt ctgctacacg ggtggaccct    960

gatcagttca ctgattttgt ggtatgaatg tttctttaac attgacttgt aaggaaagta   1020

aaatagtgga tatatgtgtg cacacatgtg tatgcgccag tagatggtat ctttaacatt   1080

catatatgct ttttctctgt ctgtattgtt gtcatgcaga ttccaaactg gtttggagga   1140

gagtccactg gggctacaaa aggcaaccca ttcacgttac cagatgccta tatggtatct   1200

cagcataaaa atgtatgtgt ggtattaatt gatttgtata ttaattaacg attggatttc   1260

caaatctttt ggtgatcaaa ttttcaaaaa actttatttt aagcgaaata tgttttaact   1320

acaatgaaat tgtatcttct tct                                           1343
```

<210> SEQ ID NO 29
<211> LENGTH: 1062
<212> TYPE: DNA
<213> ORGANISM: Glycine max

<400> SEQUENCE: 29

```
aacttgtgat tcttaatagc cttctcacgc tttttgttgt caaaggttaa ttgatgcagc     60
```

```
tttccatata gcagataagc actatataat tacgtatttc aaactacaca ttagtaatta    120

tgtcaggact tttgattatt tctgttggtc aaatttagaa tatggtacta agttaatcta    180

tagtaaatta aactaaccct ttttgagatt agatataact ctctactttt ttttaatatt    240

acattgacat ccttatacag ttatatatat atatatatat atatttaaaa taattaagga    300

agatttatat gtataaaggt gtcaatgtaa actatatatt tttaaatata acaaaaaaga    360

atagtgtagg ggtatataat aagaaaaagg taacgggtaa atttgatgaa atttcaaggg    420

gttaatataa tttaatggca ttcaactggg aaagcaatga gggatgatat tgattggtgc    480

gttgttggct tctaatgtgt ccaaagatgt gttacggaaa attgagcacc aaaagtaccc    540

atagtggttt agagaagtta ctgaaaatga aagcatgtgg tccactctgt ttgatcgatc    600

tccatttctt taaagaattg aatcaaactc tattattaac atactttctg gttccagaat    660

gaatagatat aactagactt gttttatctg acaacaaata ttattccatt tgataaggac    720

gaaacttatg ttcaaattct actttgttag ttaatgtaag aattttattg atagacgatt    780

tgaatgtatt tgagtacgaa ttttttgaat tgagactcaa attaaaatat gtctaacctg    840

atcagtgaat tattgagatc taatttacct atatattttt ttataaaaaa agaattattt    900

tatctaaacc ttttgaaaaa ttaactactt atacatactt tttcaacaac tactcctacc    960

ttagtattct gacctagggc ggctcaattt tccttttttt atttatcagt atgacatatt   1020

aacaaactcg gctgcaggac atgcaaggct ggcggtaaag ga                       1062
```

```
<210> SEQ ID NO 30
<211> LENGTH: 1095
<212> TYPE: DNA
<213> ORGANISM: Glycine max

<400> SEQUENCE: 30

aaaagttagt agaatttcgc cttaggtggt ttgggaatgc atgaagaaga cctaaagaag     60

cctcgataag aagagcagat catatggagg gcaatctatt tccttgtatc tctgtattgt    120

atagagaggt gcagtattca actcactctc tcaagttagt agttggcata ctgtgtcagt    180

ttgtaaagtt agttattgac agttgtcata actaactaac tgtttcctaa ctatctaact    240

tcataactct ataaatagag tgttgtaact caggattcat taacctccat aatattttct    300

cattccattt atcttctttc ttttctcctt tttctatgat ctaaacagag ttctaatgtg    360

atctattagt tttctattat ggtatctaga gcttggtgag atcttcaatg gctgcgaaca    420

gcaccacatt cctttccgct tcttcttttt cccaattcca tatcacataa acttgatgat    480

tcaagctttc ttctatgtcg tcaacaattt gagcctgcta tcaaaccaca caaacttaac    540

gattcgttgc taatcctcag attccacttc gatttctctc tgaagaagat caagaagttg    600

gacgtgaaaa tccagcttac gaagcatggg aaaagcaaga tcaggtgtta ttagcctgac    660

acaaatcaag gcacttgctg atgctcttgc ttcagtagga agccctataa tgattcaaga    720

gcacattgat tcaattgttg aaggtctttc tccagattat cacccgataa tcgagataat    780

ttagagtaag tttgaaaccg ttccaatcac gcaagttaaa gcacttcttc tagctcatga    840

gtcttgtctg aataacttca acgattaatt acactcatgc acaacacaga gcgaattcgc    900

attcctaaaa ttacactttg ccaaaaaagt caagttctca atcggatcct gaaagttttt    960

tctggttttc gcggtggttc tgcgtgcggt agctataata ggggtggcag cagcggcggt   1020

agtggtggcc attgtcacac tggtgcaggt caatttgcct atttccaatg ccaagtctgc   1080

tttaaatttg gtcat                                                    1095
```

<210> SEQ ID NO 31
<211> LENGTH: 508
<212> TYPE: DNA
<213> ORGANISM: Glycine max

<400> SEQUENCE: 31
ttgctcaaca tacaaaacct accacgcatt gttaatttgc aacttaatct ttcgttattc 60
tatcttgtag gcccatccat gtttgtccaa gaatgcctcg accgcttcct taatggccaa 120
gtttggcact aactgtgatg gatcaagggg ttcccgtgtg attgggtcga atttacccac 180
ctgtttaaga agttgaatta ttgcacactg acttcattga agtggaaagc attcaacaga 240
gaaggtgaaa catgcaaatc aggttacctt ctgaagatgc tcaagaatca ctgctctctc 300
atatgtaagt ccacttggag tgattacagg atcatggaaa atgtcgagtg taattctaca 360
gcacaaataa tctggcacct gtagactcaa caagacaatt tgtgtaatta ataagatggt 420
aatttccagg gcaccactga aaaaagattt gatgaatata gaattaacaa aacaagccat 480
gtacacacct cagtaggtgt gtcagctt 508

<210> SEQ ID NO 32
<211> LENGTH: 580
<212> TYPE: DNA
<213> ORGANISM: Glycine max

<400> SEQUENCE: 32
gcgtgcctgc aggtaaaaat ttatgctatt aacgaagaag atgttaatgg caggtacgtt 60
tgttattcag acatatcatg caaaatataa cttgcttagc agcttcacag aacccaatag 120
ggcatgaata atatttccgt ttaactggtt accttaccag cagacgcaaa aaacctcatg 180
ttagaccaca accaacacat gtggccagaa tcaataagca tagtaatttt actaacagag 240 aaaatttta accatgttca gtgtggcaaa tatatgctta tggggtacag taaataatga 300
taactatgct accaaagttt catgcattgg gggaggataa atgaagggaa ttgtttgaga 360
ttattttaag gagatacaaa taagagatct ctagttaaca taacaaaatc cttcaattaa 420
tgagcattta ctttttttga gctctccact tcggagtatt ttgtaagcta aattacttta 480
tacactttct ggtgcttgtc aaaattgaat tttaacattt attagaagag cagaaattta 540
taaaaacatg tcatatttgt ttttttatta aatcctttat 580

<210> SEQ ID NO 33
<211> LENGTH: 815
<212> TYPE: DNA
<213> ORGANISM: Zea mays

<400> SEQUENCE: 33
agccccctga aacattgagc tattaaaaat tagaaaacga cacaccttca gatactttct 60
gattctaaat ctaaatatga aacctcttgg tccttacttg caagtaaaag ctacatatta 120
tacaagtaat ttgatgacaa tgagctatgc agtcagcatg gaaatgtcaa aacctatctg 180
tgagaaaata tcaggagacc tagcattagg attcttttgt tttatttttc tactgattga 240
attcatgcat gacttaccta gtgcaatcta gatgaaaagg tctaacattt tccccatctt 300
aattaagcct gctacaattc acaactgggg agatagaaac tcaaactatg gcagaggcat 360
aagtgtgtat tagagtcaat ccatctacaa tgaaaagtat gctatattca taggtattgg 420
catttcaatt aatcagacaa acagtagtta ctgcacgata aaacaactga acatcaactt 480

```
tctagcattt tgctgagata ggaccccccgc agggtacata ttacaagaca ggatatgaag    540

gatggagtag catagcatta ttctagcata attatattaa cataacatga ttaggtcagg    600

tcatactcat ccggaagttg tgtttcgtca ccatagtaac tttggcagca aaacaaacta    660

gacagaacta agtagtgaaa aagaagcaca gatcgcagag agcagttcac atattttact    720

actaccaagt agcaagaacc atgtttcatc accaccctac ctttggtagc aaaacaatct    780

acatagaact aattattagt ataaaagaag ttgaa                               815
```

<210> SEQ ID NO 34
<211> LENGTH: 763
<212> TYPE: DNA
<213> ORGANISM: Zea mays

<400> SEQUENCE: 34

```
tgtaagttat ctacttattt gttccctatt ttcatttatt tatttaaagt tgagatttat     60

ccaaagtatt gttagtgtaa tgttttttct tctgccacat taggtttttg tcaatgcacg    120

gcttcatgtc tcaggagggg ctcttggggg tggtcgcatg gtagaagact cctcaagcgt    180

tgcaggttcc atattttaaa ctttctttga tgatcacatt tttgtagtat tcttttttta    240

cgtaaaacaa ttctgtggta ttcaatagca aattatacac ttcttacaag tcaacatata    300

gatttcacta tctcagtttc tttggaggtt actagcagaa aagtaattta gaaatgatta    360

atatatttta ctgaggttct caacgttgtg tttttcggtt gctggtaaat tgctcatttg    420

ctgctatagt tgattagtaa atatagcagt atttatgtca ttactggtta cttgtaatgc    480

aaaccttttt cattgaagta catgttctgt aaaatactag aacatggtca gtactttcag    540

cattggtcac taacttttat gttttatgcg agtaataata tttctatttc catgtttatc    600

tacttagttt ccatgccatg ccgccttttc agtattggac actgctgctg gagtttggtg    660

tgataccaaa tcagtagtta caactccaag gacaggaagg tatagtgcag atgcagcagg    720

tggtgatgct tctgtagagc ttacacggcg gtgcaggcac gca                      763
```

<210> SEQ ID NO 35
<211> LENGTH: 750
<212> TYPE: DNA
<213> ORGANISM: Zea mays

<400> SEQUENCE: 35

```
tgaggcaatc agtgctactt tagctgctgt aaaggctagg caagttaacg gtgagatgga     60

gcattcacct gacagggaac aatctccaga tgctgcacca agtgccaagc aaaattcaag    120

ccttataaaa ccagatcctg ctcttatgaa caattcaaca ccaccacctg ggttcggtt     180

gcaccataga gcagtgagtt gaaaaaatag ttcattttgc tgcttgttgt ttaaatttag    240

ttattctatt cttatttaga cattcagtct gtttaactta gaagtcatca catttacatg    300

aaaaatgctc ttatttgttt tgatgccagt tacatatttt ggccttgtag gttgtggtag    360

cagcagaaac tggaggtgcc ttaggtggca tggttagaca gctctcgatt gaccagtttg    420

agaatgaagg tagaagggtc atttatggca cccctgagaa tgcaactgcg gcaaggaaat    480

tgctggatcg acaaatgtct attaatagcg tgcccaaaaa ggtaatctac atttttctac    540

tattgtaaga ttactgacaa aagcaacaca tgctagaaaa ctgaaagagt tattatcata    600

atggcttctg ctaaaaaaac aagcacttca tatgatgaca ttttctctaa gatgtagatt    660

tctatattga tttgttataa ttataatctg tggcccaata attcaggtaa ttgcttctct    720

gctgaaacct cgtggttgga gcccccctgtg                                    750
```

<210> SEQ ID NO 36
<211> LENGTH: 607
<212> TYPE: DNA
<213> ORGANISM: Zea mays

<400> SEQUENCE: 36

```
cagtcactac tgtgcttttg actggaactt gtgtcgtctt atggacatca gagaagaatg      60
atggtagcag gccatctcgt gccatggcca tcaatattct tggctgaagg aagtatcaaa     120
gtggaagtat gaataccaat agcagcataa actgaagttg tgcaatgcat atgcttgttg     180
cgagaacaga taaagcagaa aactgatgat atatatccag attatatgcc agtattcttc     240
agatgttact cattttaaaa ccatgcccac ttggctgatg actcatattt tccatcaatt     300
tgaatcacag aagaaatttg atgatacatt ggttaagata tgcttatacc tgtggcaata     360
tagaccccat caaggttgag cagagagcaa gaacagcacc agttgttaca agatacctaa     420
aacaagataa gcacatgaaa acaatctcag tcagacgcac accagatcat ccatgaaaaa     480
aatgagaaga agtccttaca ttgcccagtg catcccatgt ttggcaaagg cagatgaaat     540
aggggtgtct gggtccatag caaagtatgg taccagacca acaataacaa ctgaaaccaa     600
catgtac                                                               607
```

<210> SEQ ID NO 37
<211> LENGTH: 607
<212> TYPE: DNA
<213> ORGANISM: Zea mays

<400> SEQUENCE: 37

```
cagtcactac tgtgcttttg actggaactt gtgtcgtctt atggacatca gagaagaatg      60
atggtagcag gccatctcgt gccatggcca tcaatattct tggctgaagg aagtatcaaa     120
gtggaagtat gaataccaat agcagcataa actgaagttg tgcaatgcat atgcttgttg     180
cgagaacaga taaagcagaa aactgatgat atatatccag attatatgcc agtattcttc     240
agatgttact cattttaaaa ccatgcccac ttggctgatg actcatattt tccatcaatt     300
tgaatcacag aagaaatttg atgatacatt ggttaagata tgcttatacc tgtggcaata     360
tagaccccat caaggttgag cagagagcaa gaacagcacc agttgttaca agatacctaa     420
aacaagataa gcacatgaaa acaatctcag tcagacgcac accagatcat ccatgaaaaa     480
aatgagaaga agtccttaca ttgcccagtg catcccatgt ttggcaaagg cagatgaaat     540
aggggtgtct gggtccatag caaagtatgg taccagacca acaataacaa ctgaaaccaa     600
catgtac                                                               607
```

<210> SEQ ID NO 38
<211> LENGTH: 1025
<212> TYPE: DNA
<213> ORGANISM: Zea mays

<400> SEQUENCE: 38

```
ctctagagga tccccctggt ggttgagagg tactaccagc aagtgacgat gtactgaggc      60
cagtagattg ggctggggag ctgaacccaa aaaggttgtt tccagagctc ggaaatgtaa     120
atgaaggggt tgaagcagac tgtaaacctg gtgcagtgga agtactagat ggtgcagcca     180
cagatattcc agcagcatca cttgaaggtg caactgcggt gaaagtaggc gtagatgtgg     240
cgggggaact tgaaaagctt gcaatacttg atgacacagg tgaaataaaa agttccgatg     300
```

```
atgccttgct gcttgcatct ggtgcaacag atttcacttc agcttttgta cccccctatac    360

caaatgataa ggtgctagtg ccatcagatt tagctgatgt taccaatgac aatccaaccg    420

gagcactgga agaaaaacta aatcccgtaa atgcaggaga cgatgaaata gctggactgc    480

tactggatac ggcaaatatg gaagtggaaa caggggcttc atggattcag tttgatgagc    540

ccactcttgt cctcgacctt gattctgaca aattggctgc attctctgct gcatacgcag    600

aacttgaatc tgtactttct ggattgaatg tgcttgttga gacttacttt gctgatgttc    660

ctgctgagtc ctacaagtat gttatttatg ttgctagctc acccttttct cagccattgc    720

tcctcctaga cccttttgtg atgacatcat acttgctgtt cttttgaatg caggacccta    780

acatctctga gcagtgtgac tgcttatggt tttgatcttg tccgtggaac ccaaactctt    840

gggcttgtca cgagtgctgg tttccctgct ggaaagtacc tctttgctgg tgttgtggat    900

ggacgcaaca tctgggctga tgatcttgct acatctctca gcactctcca gtctcttgag    960

gctgttgttg ggaagggtaa tcatgcttgc acttattgtc tgccataaaa ttggatttag   1020

ttaca                                                              1025
```

<210> SEQ ID NO 39
<211> LENGTH: 450
<212> TYPE: DNA
<213> ORGANISM: Zea mays

<400> SEQUENCE: 39

```
tgaaacgata gctttattta tatcactatt ggtacagtta gatagaaaag tttcaggcct     60

caatcctaag taaccgaccc cttacatatt tcgaacttct atttacaggc ctaggcaaca    120

acaagctacc tatagtgcac cggcagagcc catgctcgcc gttgcacggg ctgccgtccc    180

taacggcggc agatgtcttg cgtcgtgaca cctcccgcat ccggcgccgc ttcgcctcac    240

aatcgtccgt ggtggcttct tttgcgtcgg ccccggcccc ggcgccggca gccaccataa    300

tccccctaga cggctcaccg gacgcgggcg cgctggacta caccgtgaac gtcggctatg    360

gcacgccgga gcagcagttc ccgatgttcc tggacaccat cttcggcgtg tccctggtct    420

tgtgcaagcc gtgcgcccca ggttccagca                                     450
```

<210> SEQ ID NO 40
<211> LENGTH: 373
<212> TYPE: DNA
<213> ORGANISM: Zea mays

<400> SEQUENCE: 40

```
tcacaaattc atctttaaat tggccctaca tatgatataa ctcacactga gtaactgttg     60

atatcatatt ctaaatgact aaaagatttc agttattagc atattatgat atcacacacc    120

tttccaacaa cctcaaacgt ccattgtttc aaccggaagg ccactgcgtt tagatgatta    180

tttggcatgg aggcccagtg tgtatcacca tttaaactct gaaaaggtta gactttccct    240

gatgaaacct tctaattaag tgggtaagca aagcactatt cagtaattgt atcacctcct    300

gttctagcag gaatctccaa aatctcttca ccaggccaaa ctccgtgggg aacgtgttac    360

tcactttgtg ctt                                                       373
```

<210> SEQ ID NO 41
<211> LENGTH: 1106
<212> TYPE: DNA
<213> ORGANISM: Zea mays

<400> SEQUENCE: 41

```
gcggctccac ggccaggcac aacaagcccg gtgtctccga ccaccgagca agggtcgctc     60

ccgttctccc gcgtcccagc gcaccagccc ccgggagtcg gcacgtccgc gccgcggccc    120

aggatctcct cgtctatcct gtccagcacc gggtcgtcct cgtggaactt gcgggcgaac    180

ggcgcgtcgc tggcgaccat gcggtccagg tcctccgccg tcaagtagtg cgggtgctgc    240

ttcggagggt tgtcccacga gatgtagtgc aggtcgtggt tcaccgtcgt gttcttgaac    300

tcctccgcgt tgcacacaac ggtgtggaag tatccttccg gcgacgagat gaagtttgag    360

tagtacatga gcactgtgcg aggtaggttg tcccagcccc atatgcagta ttccacaaag    420

ggcctggaca gtgccatcca ggcagaacct gcgatgtcat aggctcatca ggtgcttcta    480

tatctgaatc agtaactgac atatatagat gcctggttat ctatatgagc tgtctggacc    540

tagagtagtg tttatatcta agctgtagtg tctgtttaag aaattggaat caattaattt    600

cctgcctaca cagagaagtg caaacctcct ttggggggag atggctaagc atggataatg    660

gatgtagaac ctgaacacca tatttatatt aatgaaaaaa cctgattttt gtgggaaaag    720

ttcattgaca cggtttcatt aatatataaa ttagtaactg acacataaaa caaggatagc    780

ctttcaaaaa ttaatggcag ctaacataaa tggatcaggg gagtaatcga gccaggaatg    840

ccttggttgg tttccagaac aggaggtcat ttttacatgc aaataaatgt gttgccatac    900

aaatgttctc tactacaggc aacaaacaaa tagaatcaca aatgtttgtt ccagcaataa    960

gatcaaacaa aataagatta tacagatgga aaggtaattt tttttaccaa ggagaatttc   1020

aggcagcgat atactacact gtacaaaaaa aaaagttaaa aaaataccac agctgtatgc   1080

actattttga agaagaccta aggtaa                                        1106
```

<210> SEQ ID NO 42
<211> LENGTH: 958
<212> TYPE: DNA
<213> ORGANISM: Zea mays

<400> SEQUENCE: 42

```
catcttgcat gcctgcagtt tctttggtag acataggtgg gcatgaaggt ggttagttct     60

ttaagattta agatgctaat ctttatgttg agttatactg tgattaaaat gaagataaac    120

atatagtagt gtggtctgtg gtgtcaggat ttgttttcat aaaaattctt tctgcatgct    180

taggtctgtt tgttaaggta tatgctagtg taaaagatgg tgctctcaga catatccatg    240

attcaaaatt aaattagtgg ttgtgacgaa gaattttgag ctgggaaggc agtgtccaca    300

ggcaattgct tagagccctg ccctgctgtg tatccttaaa attgacatga atttaggacc    360

cttgtgattt atacatctat gccaaattgc caagtgctac ttttctctat gtggaaggag    420

atacatgcat ggaaagtttt gcgcgagcct tgagtgtatc acagactatc acagctgaga    480

gggatatctg aaggatatat catgattcat gattaagtta atgtgaagat ctgactaaaa    540

ttgtgcttgc agtaaacaaa acagttctgg ttgggaacca cagatctctt aggaacattg    600

tattctgatc tgactaaaat tgtgcttgaa atgaacaaaa cagttattgg caacctcaga    660

tgcttagata tattaggaac aaatgtattc cgatctgact aaaaccgtgc ttgcagtgag    720

caaaacagtt cttgttggga acctcagatc tcttaggaac aaatgtgatc tgatctgact    780

aatattgtgc ttgtagtgat aaaaaagctc ttgttgggaa catcagatat cttaattttt    840

ttgaaaaacg caggagagct gcgcatattt atagataaga tagaagaaag ggtcttacaa    900

gagaggtaca ggttagggac acctgcaccc acacacacgc actatcaact gaaacaaa      958
```

<210> SEQ ID NO 43
<211> LENGTH: 683
<212> TYPE: DNA
<213> ORGANISM: Zea mays

<400> SEQUENCE: 43

```
tggtatgctc tctgaacttt tgctctgtaa ctgtgaccct caataaaaaa aattcagtta     60

aaggaatagg tcccgttgac cgagctcttc gattctctct gaatgcagat agctacactg    120

gtagctgtat acgcggactg ggggttcact tcgatcgaag gcattggatg ggctgggct     180

ggtgtggtgt ggctctacaa cctcgtcttc tacttcccgc tcgacctcct caagttcctc    240

atccgatacg ctctgagtgg caaagcgtgg gatcttgtca ttgagcaaag ggtgatcaat    300

ataaactgct cgttttgtca tgcacagcaa agcacagcac agcacctgtt tgagtgaatt    360

ccatgcacgc gcggtcggtg tgtcgctaat cgccggggtt ttgcagattg cgtttacaag    420

gaagaaggac ttcgggaagg aggagagggc gctcaagtgg gcacacgcgc agaggacgct    480

ccacgggctg cagccaccgg atgccaagct gttccctgac agggtgaacg agctgaatca    540

gatggccgaa gaggccaaac ggagggccga gattgcaagg taagatgttg aagtccgtgg    600

agatggtatc gcttgagggg aaagaaaggg caccgatgtc agcgtttccc atgatctctc    660

catatgcttt gggatatcta taa                                            683
```

<210> SEQ ID NO 44
<211> LENGTH: 772
<212> TYPE: DNA
<213> ORGANISM: Zea mays

<400> SEQUENCE: 44

```
cacccctacc aaatcgagca cagctcagaa gaggcagggg aggatcactc tcctaccaac     60

caaaagtcac ctcgacactg gacgtgatac aagagacaca aaacatgggc cagaagacac    120

catgcatcag acagttctga gaacttattc aacagcaaaa gtcatcttcg gatttgttgg    180

cttcctcgtt ccaccatcct ttttggcatc ttttcctgta gaacagacca cgaatccaac    240

caaaagaagc aagcataaat cacatcagta gggtcataaa agaccttgtt gttaaagcac    300

acatcattcc taaacttcca aatggcccag agaatggctc ctatgcctag aacaatcaaa    360

ttcctcgtgg ttttcttata aatgttcatc cagtcctcaa aaagagaatc caggttttga    420

ggacatctct tcacatccag ggcaacctga agaactctcc acacaaaagt ggccactggg    480

caattgagaa aaaggtgatt ggtggattcc aaaacaccac agaaacaaca atcagtcaac    540

ccaggccaat tcctttttc aggttttctt tggagataat ttttaatctt cagaacaagc     600

cacaggaaaa cttaaatttt tgaggcattc ttattttcca aagaaactta ggaactttag    660

tatgacgtca aatagatata cttggctaat aattttgaag aatttaatga ttattatttg    720

gtatcataaa tgctattatt tgattatata aaaattggtc aaacttatga tg            772
```

<210> SEQ ID NO 45
<211> LENGTH: 544
<212> TYPE: DNA
<213> ORGANISM: Zea mays

<400> SEQUENCE: 45

```
atacaatgag atggttggca tgcaaagtat tgtgttgaaa ctgataaaac attatcttat     60

atctcaaagt tctcaattgt ttacaagaag gtaaagccct gtataatttt atggcagata    120

actgcaactc ccatagaaaa tccaatgccg gaggttccca catgagtagg gtctgggaag    180
```

```
agaaaaacca aggcaagcct tcccccgcag atgaggggag gctacaaatc tcatcaacag    240

acaaaactca tccatcggcg ttggtagcgc ccagatgcca catctgggtc tggcactgga    300

cgcagcatcc accatccatt tgtcctatcc tttgatccac agttcattta atttagtcca    360

caaggaataa catatctact tctaattaat ccaagtgaaa tgggactatc ttcgtgcatt    420

cctttacctc cacatctgcc tacctcttgc accatcgcta tttctctcgt gcggaattcc    480

aaggctgggt taaaaaaaac acggaacacc cctcacccct gtcggcctgt tcttccactg    540

acgc                                                                 544
```

<210> SEQ ID NO 46
<211> LENGTH: 452
<212> TYPE: DNA
<213> ORGANISM: Zea mays

<400> SEQUENCE: 46

```
cttccatcca cgaactcccg ttctccattt ccagccatgg cggtgtcgat cgagctcacc     60

aaggagtacg gctacgtcgt gctggtgctg gtggcctatg tcttcctcaa cctttggatg    120

ggcttccagg tcggcaaggc ccgcagaaag taagctctcc gaaatctgaa tcgctcgtcg    180

ccattgttgt cttcgtttgt ctccgcccaa cttatttcat caacggacat aataatatga    240

tggtttccgc tgtgattctt ctttaggtac aaggtgttct accccaccat gtacgccatc    300

gagtcggaga acaaggacgc caagctcttc aactgcgtgc aggtgcgccc aagattctga    360

catcctctcc cctcccccgt gattaattaa ttgctcttgt gaggggttgg gactttggga    420

ggcatctaaa tttccgctgg ttcttgtggt tg                                  452
```

<210> SEQ ID NO 47
<211> LENGTH: 1064
<212> TYPE: DNA
<213> ORGANISM: Zea mays

<400> SEQUENCE: 47

```
tagctttaga gcatgtggaa atttcagctt ctggacaggc tactaacttc cctacttgca     60

cgcaagcata aggtatggtt ttaatgaaca tgttacccaa gtttgtgttt ttttagtatt    120

tcttaactaa ctttagatca actgatatat gtttgtaggt tctaatattc tcacaatgga    180

caaaagtttt ggacattctt gagtattacc tagattcaaa aggccttggg gtttgcagaa    240

ttgatggtag tgttaatttg gaagagaggc ggcgacaggt aacatgctag cctgtgccaa    300

tatattactc ctttcattcc aaattataaa atattgactt ttctagatac attacttttg    360

ctatgtatct agatatacac tcatgtggga gcctccaaca ctggatctgc cctagataca    420

cactaagtct atatgcataa caaaaagtga tgtatctaga aaagccaaaa cgtcttgtaa    480

tttgggacgt gtactatttt tctaaagaac atctaaactc tgaggatttg cactgtagtt    540

agatatttgg gtacatgtat aaatttattt cacaaaaaaa atcttttgtt actgttttct    600

catgcagata gcagagttga atgatttgaa tagcagtctg aatgtcttta ttctgagcac    660

acgggctggc ggacttggta tcaaccttac ttctgctgat acatgtatcc tttatgacag    720

tgactgggta attctctgtc aagactacta tactcatcag aaaaatgttt acaagaaagc    780

cttttttttt gctggctact ttctttggct gctgattgac ttattatgct agttctaata    840

tggtgctcgt ttactcgaac ctccagaatc ctcagatgga tcagcaggcc atggatcgat    900

gccaccggat tggtcaaaca cgcccagtac atgtatatag gctggctacc tcatattctg    960
```

ttgaggtatg cttcagtgat ccgtgttttc agacttgtca ctttggctat tgtctcaggt 1020
ttactcagct tttcaccttt gcaggaacgg atcatcaaga aagc 1064

<210> SEQ ID NO 48
<211> LENGTH: 1588
<212> TYPE: DNA
<213> ORGANISM: Zea mays

<400> SEQUENCE: 48
gggcgccggc gggtgagatc ggcaggggca tgccgccgtt ggccccggcg gcggtagaga 60
atcctgatga tgctgcagag tggtgcaacg gcacgtgagg ggagccctgc gcttgccatg 120
cccatgaggg gaatggctgg gcgcccagct caggccttcg ctccaccggc ctttcctgga 180
cctgcacgat atcgcagcag cacgagcatg agctttgttt gtcaggtttt gaccacagtg 240
aacgtttcca cctttaagtc gttcacagga aacagagcga acaaacaacc aagattggat 300
atcggcgagc atgattaatc tttcatgatt ctgttttaat taattgattg attttaacgt 360
atgtgcagca caatgaagac ttgatgctag ctctatttcc cgtaaaaatt cagagaatcc 420
tcaggactac agctgcagca cgtgatccct gatcagcgta ctaaaagata catcccatgt 480
tatgtcaaga aactgcgacc caacaaccgc gactgcggtg tttcaaaaga tggaaagtgg 540
cagaacggcc tggtcgaaac accaaccagt ccacacacca aacagtacct gccattatag 600
taaggagtac cattgccccc cacccccccc aaaaaaaaca gaaaaagaag tgctgtatag 660
tatttttcca aggagcaaga cgtttcataa gaaatttcta aacaagctaa cagtaacagg 720
ttggtaggga atcaatctac aagtaaatgt ctatctagct gctctcagtc aaaaaggtta 780
gacatgtcgc acatatatat tcggcttgtt tctttcccat tatttccttt ttggaacaca 840
ggtcatgttc agctaaccat cctggattct acgatagttt ggaataactg atggagtatg 900
tagtaacaga catttgcatg tgtaagtgta acaaagggat cttggcgata cctggtggtt 960
cggaaagaag ccatgacaag ctgacgagta caagcgctga tggtgagatg acactgctgg 1020
gttttggtga tacccgggcc aaggggatga tgagctcatt ggctacagca gcagcaggtg 1080
aaaggagcaa acactgtgag atcaataata gttgtaggac ctggaccacg aattaatatc 1140
gatctccccc aaccatatgc caatcaaata gtcctatgaa tctttgtagg ctaggagtta 1200
ctagtaggaa ctagtatcag aggtccaaga ttctacaaag acaattcaac cgacagttgc 1260
ttccatctta agattttaat tttttttcta gatacctctt taggcaccat aagtaaaaag 1320
ctatatactg gaaaattgaa cgggtggttt tacctgagaa gccatcgtat ttgaagattc 1380
aggggaatca catgttggct ggaggccagc taaggtattg tcccttttgg ggtcttgcac 1440
attaggctgt gaaatccgca aatccaaatc aatggcatca ccatcatcaa ttgctgacaa 1500
cgtagagaga accatgagat acacctcaga tactatatat attaaaaaaa agaacggatg 1560
acaaggccga gtgtaatacc ctcggttt 1588

<210> SEQ ID NO 49
<211> LENGTH: 784
<212> TYPE: DNA
<213> ORGANISM: Zea mays

<400> SEQUENCE: 49
aacataattt catgtactgt tcgtacagag attatcttta gagagaatag taagtactac 60
cttcgttctt gaatatttat catctgctag tttaatttta aactaaaacg tgataaataa 120
aaaaaacgaa gagggtatct tctatcttgt aataccaacc acgtgaagac cttcactcca 180

```
cggttgtttt gcctttttag attatattaa aactttgccc atacaaaaca gtttcttagg    240

gaaatttcca gatttatctc actcgcaatt accaactggc catcgttatt ttttagaacg    300

atatcttgca atcttctaag ctgactctgt aaatcttcac gtagccatct cctaaaaatg    360

aggctctagt ttttatattt catggcttca actgaacaat cacggtcctc gttttttttta    420

aaaaaaatga gaaaagtgtg tctttaaagt aacctatagc cacaccatct agtatgccaa    480

aaaaatggtg gatttttcat tggccgacac cgtagacctg ctgcttaagt aaatatatct    540

ggtttggggt taattagaag tatgccactc caaatttaaa gagttataaa gtagtttatt    600

ttcatgtcgc tcaatgacat caaaatgaat tacctatcta attttataaa aacagggtga    660

caagtatgta attaatcttt tttttcttag ctaggtttag tgatcttagt ccatctaatc    720

aaatgatatt tccctcttcc aaaaaaaacg ctttctagca ctatccatct ttccaataga    780

tgtc                                                                 784
```

<210> SEQ ID NO 50
<211> LENGTH: 802
<212> TYPE: DNA
<213> ORGANISM: Zea mays

<400> SEQUENCE: 50

```
tgctgcgtcg tcgtgttgtt acgatcgtcc tttttttttt gaaaatttat tgaaggcccg     60

tgcttcttct tctcttcttc ttttccttct ccactgtttt cctcgcatgc tacatgacag    120

tctctctctc tcgttaactc tgttggtgtt cttattattt gatccggatg caagtaatac    180

tatacaaaca ggaatcggga atgcacgctc ccaatttttg acgcctccat gcatgtagtg    240

gcggagttcc gtaaaattaa cgtccgagat gtactattct atcttttgat ttttttttttc    300

gtgttttatt taaaaataaa cagcggatga taaatattta ataacggaga gtaacattta    360

aaacaatcca gttaaactat gacaagtagg gaaagtggat tagatattcg ggaacaatta    420

cttacaatag aggagaatca cgagcacatg gcagcagaca gtcaacactc aggacacaac    480

gttcgccgct caggtggccg ttgttcattg gccaaggagg cactctgcac tcgcctatga    540

ataacaaaaa aagataatca agttgagaaa gttatatagc ttggaagaag atgtaatgac    600

aggggtggat ttgggcggtg gcatggcgcc agccccccgcg cgcgacactg ctatagggtc    660

gcagggaggc tggaggcgga tggtggaggc cgatgccaga ctggcggtgg tggatgcccc    720

gagtcaagcc cgccccgacc gcctcggagg gttgctggtt tgttcctcat tgccgaattc    780

cccggaagcc cttaaggctt tt                                             802
```

<210> SEQ ID NO 51
<211> LENGTH: 793
<212> TYPE: DNA
<213> ORGANISM: Zea mays
<220> FEATURE:
<221> NAME/KEY: unsure
<222> LOCATION: (1)..(793)
<223> OTHER INFORMATION: n=a,g,c,or t

<400> SEQUENCE: 51

```
aaagtaagca aaactaagct gaaatctgca agaagcagta ttgagattac caaaccaaca     60

agatcctgca gttaagttca acagaaccaa gatcagcatt cagcacaaaa tgaactgatt    120

cataatcact ctgtggacag taacagtggc agagaaagac ctgatgccca actggtttcg    180

aattgtgcaa gatatgagaa aatgggtaaa acaaatctct cctgtctttt agtgtcctta    240
```

```
agctattact attgagaact ccaccagtga tccttttgcg cattagagca tccttaatcc    300

tggactgact tagttgagta tcagcgagca tgttctgtgt gctgcatagt ataataataa    360

gccatcataa ataataatga tgataaacga aatcaataac ataaaacaca taataactca    420

cgtgttctgt gtgctgcgta gtataataat aagccatcat aaataataat gatgataaac    480

gaaatcaata acataaaaca cataataact cacggtgtgt gttgctctat ttttactcta    540

gggcttccat caggttcggt aagtgcagct tctccttcaa cagcataaac aagaagacca    600

agttggcagt accctaatgc tgtagcttgg aaccaggcaa gatcaacacg gataccattc    660

tcagctaaag agggatttgc atgagattca agccagttga tgaccggaag aaacgttact    720

ttcagatttc caccacggac caaacgcagg gggatnctnt agagtcgaac ctgcaggnnc    780

agcaagtcat agg                                                       793
```

<210> SEQ ID NO 52
<211> LENGTH: 748
<212> TYPE: DNA
<213> ORGANISM: Zea mays

<400> SEQUENCE: 52

```
atcattttc aaccaagtaa tggagatcgc tttttatttt tagtatgtcg catcgttggc      60

tagagctttg atctaccttc atggcaagca tgttatccat cgggacatta aaccagagaa    120

tcttttagtt ggagttcagg tacttgcatt gtgttctttt ttggtatccc tctggcaccg    180

ggtctgctct gcctcatctg gaagactgga actatatgct tgctttacat cgtcgtctgt    240

ttccttggaa cagggcgaga tcaaaattgc cgactttggc tggtctgtgc acaccttcaa    300

cagaagacgg actatgtgcg gaactctgga ttacctgcca cctgaaatgg gtactttgct    360

agccatttac ctccagttat gaactagttc aatgggtttt gagaattccc acagcagtac    420

ctagctgctt tccttggctc tgaaacctgt tgtggtttat ccagtggaga aggcagaaca    480

tgattaccat gttgatatat ggagccttgg tgttctgtgc tatgagttcc tttacggggt    540

cccacctttc gaagctaagg agcactcaga aacctacaga aggtaactcc acaactctgg    600

gatcttagta tgtcgtccct aacttgccga tatcttgccc tagattattt cctgtggctt    660

ttgacttttg agctatgctc tgataactgt gaggaaactt ttgaagttgc atatagtgct    720

agtgtagcaa agagagagca ctatattg                                       748
```

<210> SEQ ID NO 53
<211> LENGTH: 610
<212> TYPE: DNA
<213> ORGANISM: Zea mays

<400> SEQUENCE: 53

```
atattcaaaa gggaaacgaa gatggcttgt ttattagttc agttgcctct agctcaaatc     60

tgtgggcttt aattatggat gctggcactg gctttacatc tcaagtatac gaactttcta    120

attactttct tcacaaggta agcaatcaat tctgttgact tcaaagatct gtaagggtcc    180

ttcccctttt ttcttcttaa tataatgata ttcagctctc ctgcttattt gagagaaaaa    240

aaccttcaaa gatatgtaag ggttcttcct ctttgtaata gggtctttac ccttcctttt    300

cttcttctta atataatgat acacaatttc tcctgcttat tcgagaaaaa aattgagaga    360

aaaaaccttc aaaaatttac tgttctttgt ttatgattgt acgccaacac ttcactgatt    420

atacatcctc aatgatgtct cattgtcatt cgcatgcttg tactgtgtta ggaatggata    480

atggaacagt gggagagaaa tttctatatc actgcactgg ctggggcgaa taatggaagc    540
```

```
tctttggtga ttatgtcaag aggtaattaa tgtaaatgtt tgagcttgat gcttagactg    600

caggcatgca                                                           610
```

<210> SEQ ID NO 54
<211> LENGTH: 883
<212> TYPE: DNA
<213> ORGANISM: Zea mays

<400> SEQUENCE: 54

```
atttgaatag gatacatatg aaaaaagaga aattaaaggc ctgtttggtt cactacctca     60

gttgccacaa tttgcctaac ttttctgcct gaggttagtt attcaattcg aacgactaac    120

cttaggcaaa gtgtggcaca tttagccaca aaccaaacag gccctaagtg tttgctcagc    180

caaacatcgt gtatcagctt gaaatccaaa atatgtttgg caaaacatag cacatttatc    240

aagaaatcat agaaggcaaa atgcaatatg ctaatggaaa aggctcacag gtgactacga    300

tatctctcaa caggatatac aatgcttgag atggagttcg ccatactcag aaatttgttt    360

gacatgtgtc attttataat tttattttag aagctaggat tcagacttca actggagtag    420

atcaagtcaa tacataaaca gtattctttc atactaagaa atatcacctt gtaagattcc    480

tcaagcctgt ccttgtattt ttcaaccaac agctctttac tcaatgccag atctctttcc    540

actactgcct ctgtctcaaa ctattaagag acaagagaac acattactct atctattcaa    600

aacaattcct gtaatcaagt gataatataa ctataaccaa ctaaacatca tgaaaaaatt    660

gcagtgcaat acctgaataa caatgtgagg atacaatgtt tgtcctttac ggattggtgg    720

atcaagagtg ataacaacaa atgtatgagg attgtttgac tgcaaaggtc aaccatgcaa    780

tgagtttagt tacatgtcac aatgtaatac tatgtacaat aataaagcac aagcctcaac    840

catatgatac caaggaacag aaaccttttg gcaaaaagga aag                      883
```

<210> SEQ ID NO 55
<211> LENGTH: 24
<212> TYPE: DNA
<213> ORGANISM: Glycine max

<400> SEQUENCE: 55

```
tgcttgcttt ggacctacac aaaa                                            24
```

<210> SEQ ID NO 56
<211> LENGTH: 24
<212> TYPE: DNA
<213> ORGANISM: Glycine max

<400> SEQUENCE: 56

```
aaaagcccaa aaggaagagt ggag                                            24
```

<210> SEQ ID NO 57
<211> LENGTH: 24
<212> TYPE: DNA
<213> ORGANISM: Glycine max

<400> SEQUENCE: 57

```
gcgatgacct tgtatggggt agac                                            24
```

<210> SEQ ID NO 58
<211> LENGTH: 24
<212> TYPE: DNA
<213> ORGANISM: Glycine max

<400> SEQUENCE: 58
ccatgccctg attcattcat cata 24

<210> SEQ ID NO 59
<211> LENGTH: 1249
<212> TYPE: DNA
<213> ORGANISM: Glycine max

<400> SEQUENCE: 59
cagactctag tgactaccac cttcactctc ctcaagcatt tcagcctctt ccccgctcag 60
actccttagc tttgggagcc aaattatccc ttacgttctc gacttcaacc atatgtgata 120
gctgcctatg ataccatggc tacttcccgt tagttcttta tctttccttt ccgctttatt 180
ccatgcctta ccgatcctct gaagtgtctt tgcattagct tcattgaaac ctcacgcgat 240
gaaaggtgtg atggtctcct ccgatggcgc acttctcata gggtaaccta attgtcttac 300
gaccaacata ggattataat taatacaacc cctcgtccct ataaaaggga catttggaaa 360
tccttcacat aagcataaca ctcctacccc tctttctttc cactgtggga accaactaat 420
ggacgctcct atcatgcctg ccaagagttc ttcccaattt gcctcgtcct ttcctgagca 480
catgcgatga ccttgtatgg ggtagacaga tctactttca tgattgaaga cgtgggatac 540
caaccacaca taaagagcag gcgcacaaca gaaaatcctc gtagtgctct tcttgcatct 600
taagtcaaat gtatcataca cttatgctaa aacaacaatg atcgggcttt ccttgctatg 660
gtgataagca agaaaagcat cgattgctac tagatccacc aactcgtcta cattcgaaaa 720
tagtactatc ccaaacacta gcagtgctaa tacgtcgatg aatgatgccc actctccttg 780
gctggccaga gtttccgcct tctcctccaa tcacttcctt ggtattcccc ctaccctatt 840
cctactttgc ttcactcagt ctaattctca tttcgagatc ttgacaactc ctgctattct 900
cgccatagaa ggatagtacc cagaaaaaag gtatggcttc cttcctccta tcgggcatcc 960
taagatccct tcgaactcct ctatggttgg tgctaactga aagtccccaa aagtgaagca 1020
tctgagtgat tggtcatagt attgggtgag agatgcgatg gcttcaacga acacttctat 1080
catcaccaga tcccaaatct tcccatatac cttgttgaag gactgacgtt gagctcgatc 1140
catccgatgc cccagttttc gcaagatgac tacttctaga ttcttgagtt cgacacgata 1200 gaacctttc ttaaaagaca gtgcttgtct gaccccatct catcagact 1249

<210> SEQ ID NO 60
<211> LENGTH: 25
<212> TYPE: DNA
<213> ORGANISM: Glycine max

<400> SEQUENCE: 60
cgttctcgac ttcaaccata tgtga 25

<210> SEQ ID NO 61
<211> LENGTH: 25
<212> TYPE: DNA
<213> ORGANISM: Glycine max

<400> SEQUENCE: 61
gcatggaata aagcggaaag gaaag 25

<210> SEQ ID NO 62
<211> LENGTH: 17
<212> TYPE: DNA
<213> ORGANISM: Glycine max

```
<400> SEQUENCE: 62

ccatggtatc ataggca                                                    17


<210> SEQ ID NO 63
<211> LENGTH: 17
<212> TYPE: DNA
<213> ORGANISM: Glycine max

<400> SEQUENCE: 63

ccatggtatc gtaggca                                                    17
```